(12) United States Patent
Al-Ali et al.

(10) Patent No.: US 9,161,696 B2
(45) Date of Patent: Oct. 20, 2015

(54) MODULAR PATIENT MONITOR

(75) Inventors: Ammar Al-Ali, San Juan Capistrano, CA (US); Paul Jansen, San Clemente, CA (US); Massi Joe E. Kiani, Laguna Niguel, CA (US); Anand Sampath, Corona, CA (US)

(73) Assignee: MASIMO CORPORATION, Irvine, CA (US)

( * ) Notice: Subject to any disclaimer, the term of this patent is extended or adjusted under 35 U.S.C. 154(b) by 8 days.

(21) Appl. No.: 12/641,087

(22) Filed: Dec. 17, 2009

(65) Prior Publication Data

US 2010/0261979 A1    Oct. 14, 2010

Related U.S. Application Data

(63) Continuation-in-part of application No. 11/903,746, filed on Sep. 24, 2007, now Pat. No. 8,840,549.

(60) Provisional application No. 60/846,471, filed on Sep. 22, 2006.

(51) Int. Cl.
*A61B 5/00* (2006.01)
*G06F 19/00* (2011.01)
(Continued)

(52) U.S. Cl.
CPC .............. *A61B 5/0205* (2013.01); *A61B 5/0002* (2013.01); *A61B 5/14542* (2013.01);
(Continued)

(58) Field of Classification Search
CPC .... A61B 5/0205; A61B 5/0022; A61B 5/411; A61B 5/743; A61B 5/01; A61B 5/7445; A61B 5/7267; A61B 5/7275; A61B 5/7282; A61B 5/7475; A61B 5/002; A61B 5/7225; A61B 5/0533; A61B 5/11; A61B 5/14532

USPC .......................... 600/300–301; 361/679, 681
See application file for complete search history.

(56) References Cited

U.S. PATENT DOCUMENTS 3,646,606 A   2/1972   Buxton et al.
3,978,849 A   9/1976   Geneen
(Continued)

FOREIGN PATENT DOCUMENTS

EP        735499        10/1996
EP    2 335 569 A2      6/2011
(Continued)

OTHER PUBLICATIONS

PCT International Search Report & Written Opinion, App. No. PCT/US2012/060109, App. Date: Dec. 10, 2012, in 17 pages.
(Continued)

*Primary Examiner* — William Thomson
*Assistant Examiner* — Marie Archer
(74) *Attorney, Agent, or Firm* — Knobbe, Martens, Olson & Bear LLP

(57) ABSTRACT

A modular patient monitor has a docking station configured to accept a handheld monitor. The docking station has standalone patient monitoring functionality with respect to a first set of parameters. At least some of the first parameter set are displayed simultaneously on a full-sized screen integrated with the docking station. The handheld monitor also has standalone patient monitoring functionality with respect to a second set of parameters. At least some of the second set of parameters are displayed simultaneously on a handheld-sized screen integrated with the handheld monitor. The docking station has a port configured to accept the handheld monitor. While the handheld monitor is docket in the port, the docking station functionally combines the first set of parameters and the second set of parameters, and at least some of the combined first and second sets of parameters are displayed simultaneously on the full-sized screen.

20 Claims, 21 Drawing Sheets

(51) Int. Cl.
 *A61B 5/0205* (2006.01)
 *A61B 5/145* (2006.01)
 *A61B 5/1455* (2006.01)

(52) U.S. Cl.
 CPC .............. *A61B5/742* (2013.01); *A61B 5/7445* (2013.01); *G06F 19/3406* (2013.01); *G06F 19/3412* (2013.01); *A61B 5/1455* (2013.01); *A61B 5/743* (2013.01); *A61B 2560/0431* (2013.01); *A61B 2560/0443* (2013.01); *A61B 2560/0456* (2013.01)

(56) References Cited

U.S. PATENT DOCUMENTS

| | | |
|---|---|---|
| 4,108,166 A | 8/1978 | Schmid |
| 4,231,354 A | 11/1980 | Kurtz et al. |
| 4,589,415 A | 5/1986 | Haaga |
| 4,662,378 A | 5/1987 | Thomis |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Schimizu |
| 5,377,676 A | 1/1995 | Vari et al. |
| 5,400,794 A | 3/1995 | Gorman |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,685,299 A | 11/1997 | Diab et al. |
| 5,685,314 A | 11/1997 | Geheb et al. |
| 5,687,717 A | 11/1997 | Halpern et al. |
| 5,724,580 A | 3/1998 | Levin et al. |
| 5,724,983 A | 3/1998 | Selker et al. |
| 5,725,308 A | 3/1998 | Smith et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer et al. |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,822,544 A | 10/1998 | Chaco et al. |
| 5,822,546 A | 10/1998 | George |
| 5,823,950 A | 10/1998 | Diab et al. |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,934,925 A | 8/1999 | Tobler et al. |
| 5,940,182 A | 8/1999 | Lepper, Jr. et al. |
| 5,942,986 A | 8/1999 | Shabot et al. |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| 6,168,563 B1 | 1/2001 | Brown |
| 6,171,237 B1 | 1/2001 | Avitall et al. |
| 6,183,417 B1 | 2/2001 | Gehab et al. |
| 6,184,521 B1 | 2/2001 | Coffin, IV et al. |

(56) References Cited

U.S. PATENT DOCUMENTS

| | | |
|---|---|---|
| 6,185,448 B1 | 2/2001 | Borovsky |
| 6,195,576 B1 | 2/2001 | John |
| 6,206,830 B1 | 3/2001 | Diab et al. |
| 6,221,012 B1 * | 4/2001 | Maschke et al. ............ 600/301 |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,354,235 B1 | 3/2002 | Davies |
| 6,360,114 B1 | 3/2002 | Diab et al. |
| 6,364,834 B1 | 4/2002 | Reuss et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 10/2002 | Boesen |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,544,174 B2 | 4/2003 | West et al. |
| 6,551,243 B2 | 4/2003 | Bocionek et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,639,668 B1 | 10/2003 | Trepagnier |
| 6,640,116 B2 | 10/2003 | Diab |
| 6,641,533 B2 | 11/2003 | Causey et al. |
| 6,643,530 B2 | 11/2003 | Diab et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,751,492 B2 | 6/2004 | Ben-haim |
| 6,760,607 B2 | 7/2004 | Al-Ali |
| 6,770,028 B1 | 8/2004 | Ali et al. |
| 6,771,994 B2 | 8/2004 | Kiani et al. |
| 6,790,178 B1 | 9/2004 | Mault et al. |
| 6,792,300 B1 | 9/2004 | Diab et al. |
| 6,795,724 B2 | 9/2004 | Hogan |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,063,666 B2 | 6/2006 | Weng et al. |
| 7,067,893 B2 | 6/2006 | Mills et al. |
| 7,079,035 B2 | 7/2006 | Bock et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |

(56) References Cited

U.S. PATENT DOCUMENTS

| | | |
|---|---|---|
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,256,708 B2 | 8/2007 | Rosenfeld |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,382,247 B2 | 6/2008 | Welch et al. |
| 7,383,070 B2 | 6/2008 | Diab et al. |
| 7,395,216 B2 | 7/2008 | Rosenfeld |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,590,950 B2 | 9/2009 | Collins et al. |
| 7,596,398 B2 | 9/2009 | Al-Ali et al. |
| 7,597,665 B2 | 10/2009 | Wilk et al. |
| 7,612,999 B2 | 11/2009 | Clark et al. |
| 7,618,375 B2 | 11/2009 | Flaherty |
| D606,659 S | 12/2009 | Kiani et al. |
| 7,639,145 B2 | 12/2009 | Lawson et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| RE41,317 E | 5/2010 | Parker |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,820,184 B2 | 10/2010 | Stritzker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |

(56) References Cited

U.S. PATENT DOCUMENTS

| | | |
|---|---|---|
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Al-Ali et al. |
| 7,991,463 B2 | 8/2011 | Kelleher et al. |
| 7,991,625 B2 | 8/2011 | Rosenfeld |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,294,716 B2 | 10/2012 | Lord et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 8,326,649 B2 | 12/2012 | Rosenfeld |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,600,467 B2 | 12/2013 | Al-Ali et al. |
| 8,600,777 B2 | 12/2013 | Schoenberg |
| 8,606,342 B2 | 12/2013 | Diab |
| 8,620,678 B2 | 12/2013 | Gotlib |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |

(56) References Cited

U.S. PATENT DOCUMENTS

| | | |
|---|---|---|
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 2001/0011355 A1 | 8/2001 | Kawai |
| 2001/0031922 A1 | 10/2001 | Weng et al. |
| 2001/0046366 A1 | 11/2001 | Susskind |
| 2002/0045836 A1 | 4/2002 | Alkawwas |
| 2002/0052311 A1 | 5/2002 | Solomon et al. |
| 2002/0063690 A1 | 5/2002 | Chung et al. |
| 2002/0140675 A1 | 10/2002 | Ali et al. |
| 2002/0177758 A1 | 11/2002 | Schoenberg |
| 2002/0198445 A1 | 12/2002 | Dominguez et al. |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2004/0013647 A1 | 1/2004 | Solomon et al. |
| 2004/0073095 A1 | 4/2004 | Causey et al. |
| 2004/0090742 A1 | 5/2004 | Son et al. |
| 2004/0122787 A1 | 6/2004 | Avinash et al. |
| 2004/0126007 A1 | 7/2004 | Ziel et al. |
| 2004/0147818 A1 | 7/2004 | Levy et al. |
| 2004/0152957 A1 | 8/2004 | Stivoric et al. |
| 2004/0179332 A1* | 9/2004 | Smith et al. ............ 361/681 |
| 2004/0186357 A1 | 9/2004 | Soderberg et al. |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0254431 A1 | 12/2004 | Shehada et al. |
| 2004/0254432 A1 | 12/2004 | Shehada et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0065417 A1* | 3/2005 | Ali et al. ............ 600/323 |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0125256 A1 | 6/2005 | Schoenberg |
| 2005/0164933 A1 | 7/2005 | Tymianski et al. |
| 2005/0191294 A1 | 9/2005 | Arap et al. |
| 2005/0277872 A1 | 12/2005 | Colby et al. |
| 2006/0058647 A1 | 3/2006 | Strommer et al. |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0021675 A1 | 1/2007 | Childre et al. |
| 2007/0027368 A1 | 2/2007 | Collins et al. |
| 2007/0032733 A1 | 2/2007 | Burton |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0088406 A1 | 4/2007 | Bennett et al. |
| 2007/0096897 A1 | 5/2007 | Weiner |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0163589 A1 | 7/2007 | DeVries et al. |
| 2007/0185390 A1 | 8/2007 | Perkins et al. |
| 2007/0232941 A1 | 10/2007 | Rabinovich |
| 2007/0244724 A1 | 10/2007 | Pendergast et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0053438 A1 | 3/2008 | DeVries et al. |
| 2008/0058657 A1 | 3/2008 | Schwartz et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0097167 A1 | 4/2008 | Yudkovitch et al. |
| 2008/0099366 A1 | 5/2008 | Niemiec et al. |
| 2008/0108884 A1 | 5/2008 | Kiani |
| 2008/0119412 A1 | 5/2008 | Tymianski et al. |
| 2008/0138278 A1 | 6/2008 | Scherz et al. |
| 2008/0171919 A1 | 7/2008 | Stivoric et al. |
| 2008/0194918 A1 | 8/2008 | Kulik et al. |
| 2008/0208912 A1 | 8/2008 | Garibaldi |
| 2008/0221396 A1 | 9/2008 | Garces et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0319275 A1* | 12/2008 | Chiu et al. ............ 600/300 |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0052623 A1 | 2/2009 | Tome et al. |
| 2009/0054735 A1 | 2/2009 | Higgins et al. |

(56) References Cited

U.S. PATENT DOCUMENTS

| | | |
|---|---|---|
| 2009/0054743 A1 | 2/2009 | Stewart |
| 2009/0062682 A1 | 3/2009 | Bland et al. |
| 2009/0069642 A1 | 3/2009 | Gao et al. |
| 2009/0119330 A1 | 5/2009 | Sampath et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0247984 A1 | 10/2009 | Lamego et al. |
| 2009/0264778 A1 | 10/2009 | Markowitz et al. |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0069725 A1 | 3/2010 | Al-Ali |
| 2010/0125217 A1 | 5/2010 | Kuo et al. |
| 2010/0144627 A1 | 6/2010 | Vitek et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0261979 A1 | 10/2010 | Kiani |
| 2010/0298659 A1 | 11/2010 | Mccombie et al. |
| 2010/0298661 A1 | 11/2010 | Mccombie et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2011/0001605 A1 | 1/2011 | Kiani et al. |
| 2011/0021930 A1 | 1/2011 | Mazzeo et al. |
| 2011/0023130 A1 | 1/2011 | Gudgel et al. |
| 2011/0028809 A1 | 2/2011 | Goodman |
| 2011/0046495 A1 | 2/2011 | Osypka |
| 2011/0080294 A1 | 4/2011 | Tanishima et al. |
| 2011/0082711 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0118573 A1 | 5/2011 | Mckenna |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0257544 A1 | 10/2011 | Kaasinen et al. |
| 2011/0295094 A1 | 12/2011 | Doyle |
| 2012/0004579 A1 | 1/2012 | Luo et al. |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0101353 A1 | 4/2012 | Reggiardo et al. |
| 2012/0116175 A1 | 5/2012 | Al-Ali et al. |
| 2012/0123799 A1 | 5/2012 | Nolen et al. |
| 2012/0136221 A1 | 5/2012 | Killen et al. |
| 2012/0179006 A1 | 7/2012 | Jansen et al. |
| 2012/0197619 A1 | 8/2012 | Namer Yelin et al. |
| 2012/0209082 A1 | 8/2012 | Al-Ali |
| 2012/0209084 A1 | 8/2012 | Olsen et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0265039 A1 | 10/2012 | Kiani |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0294801 A1 | 11/2012 | Scherz et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0274571 A1 | 10/2013 | Diab et al. |
| 2013/0296672 A1 | 11/2013 | O'Neil et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |

(56) References Cited

U.S. PATENT DOCUMENTS

| | | |
|---|---|---|
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali |
| 2015/0097701 A1 | 4/2015 | Al-Ali et al. |
| 2015/0112151 A1 | 4/2015 | Muhsin et al. |

FOREIGN PATENT DOCUMENTS

| | | |
|---|---|---|
| EP | 2766834 | 8/2014 |
| EP | 2811894 | 12/2014 |
| JP | 2014/533997 | 12/2014 |
| WO | WO 98/29790 | 7/1998 |
| WO | WO 99/13766 | 3/1999 |
| WO | WO/2004/056266 | 7/2004 |
| WO | WO/2004/059551 | 7/2004 |
| WO | WO 2013/056160 | 4/2013 |
| WO | WO 2013/119982 | 8/2013 |
| WO | WO 2015/054665 | 4/2015 |

OTHER PUBLICATIONS

Wachter, S. Blake; Journal of the American Medical Informatics Association; The Employment of an Iterative Design Process to Develop a Pulmonary Graphical Display; vol. 10, No. 4, Jul./Aug. 2003; pp. 363-372.

US 8,845,543, 9/2014, Diab et al. (withdrawn).

Capuano et at. "Remote Telemetry—New Twists for Old Technology." Nursing Management. vol. 26, No. 7. Jul. 1995.

Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.

PCT International Preliminary Report on Patentability for Application No. PCT/US2012/060109, dated Apr. 24, 2014.

PCT International Search Report & Written Opinion, App. No. PCT/US2014/060177, dated Dec. 19, 2014.

PCT International Search Report and Written Opinion, App. No. PCT/US2013/025384, dated Aug. 6, 2013.

Extended European Search Report for European Application No. 10195398.2 dated Jul. 5, 2012.

* cited by examiner

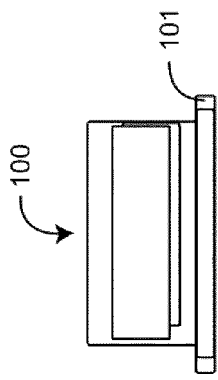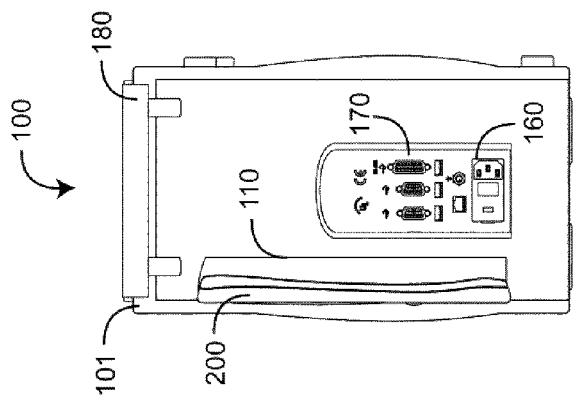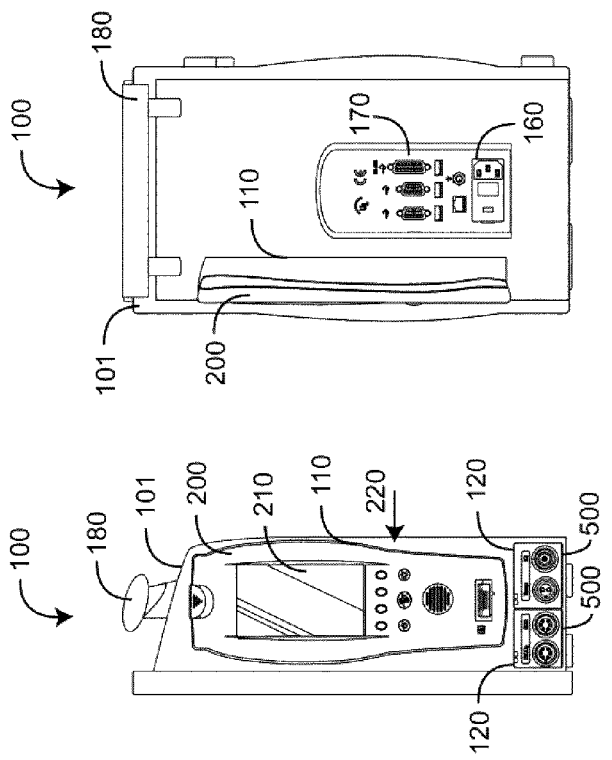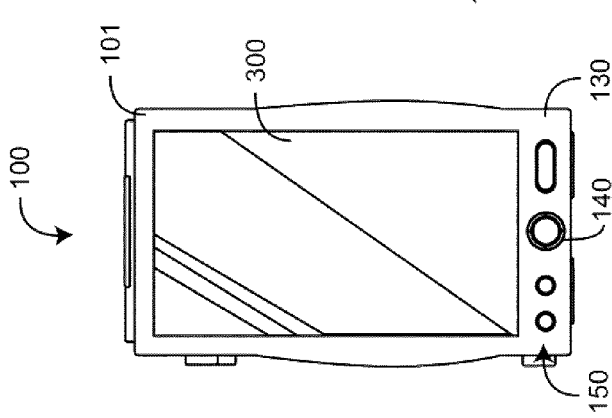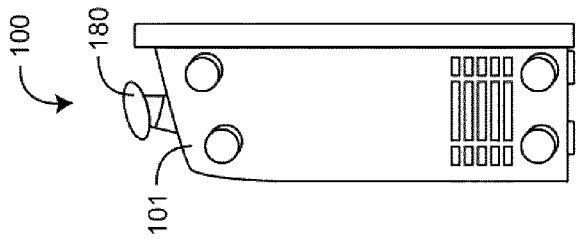

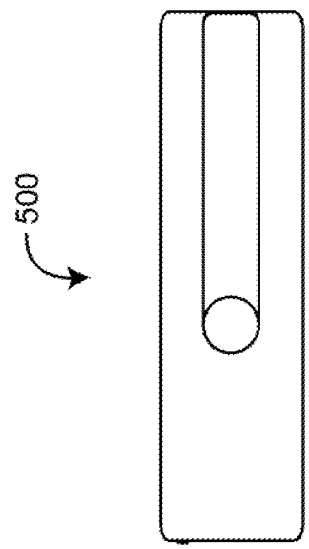
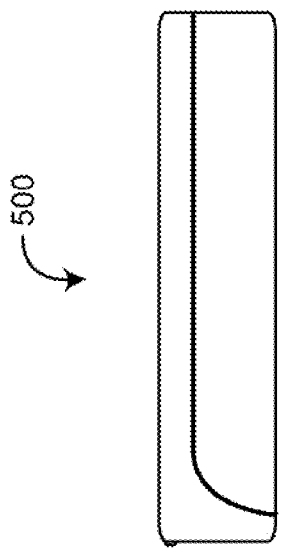
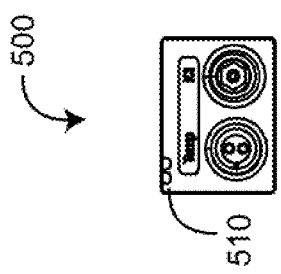

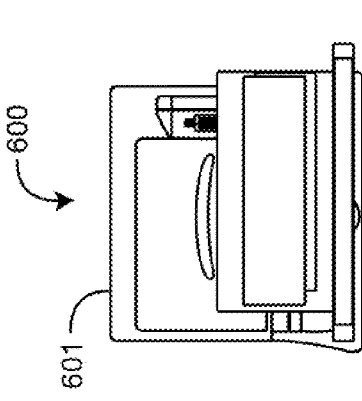
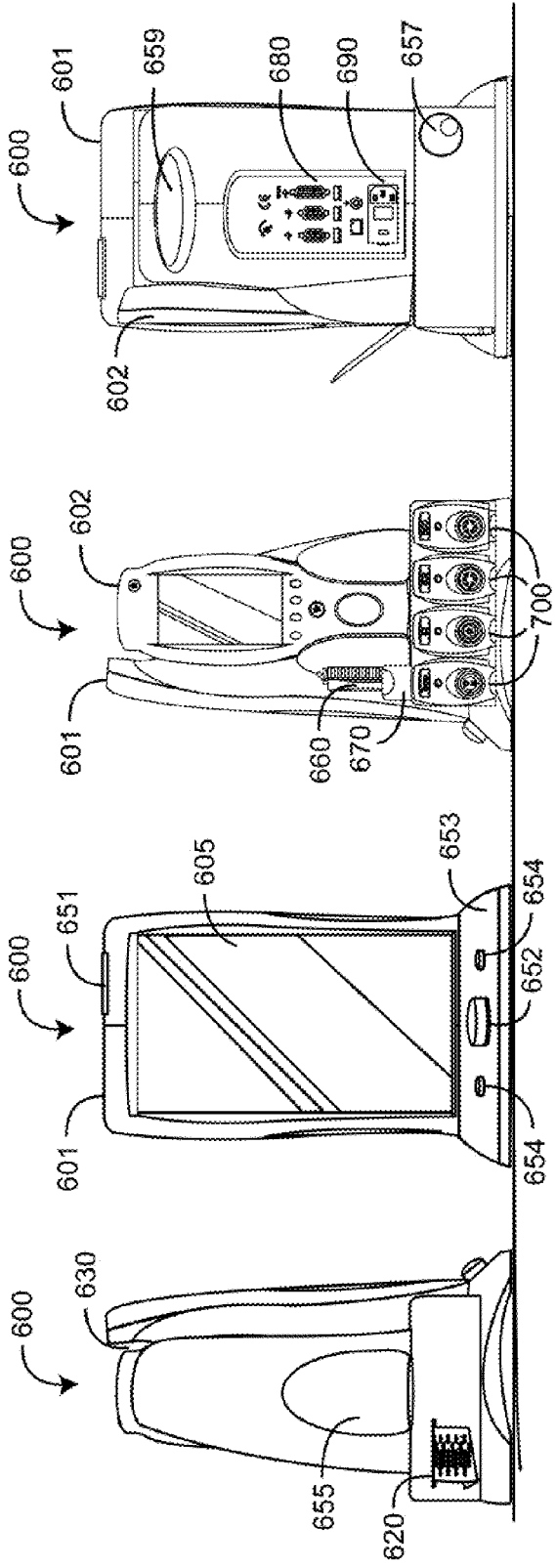

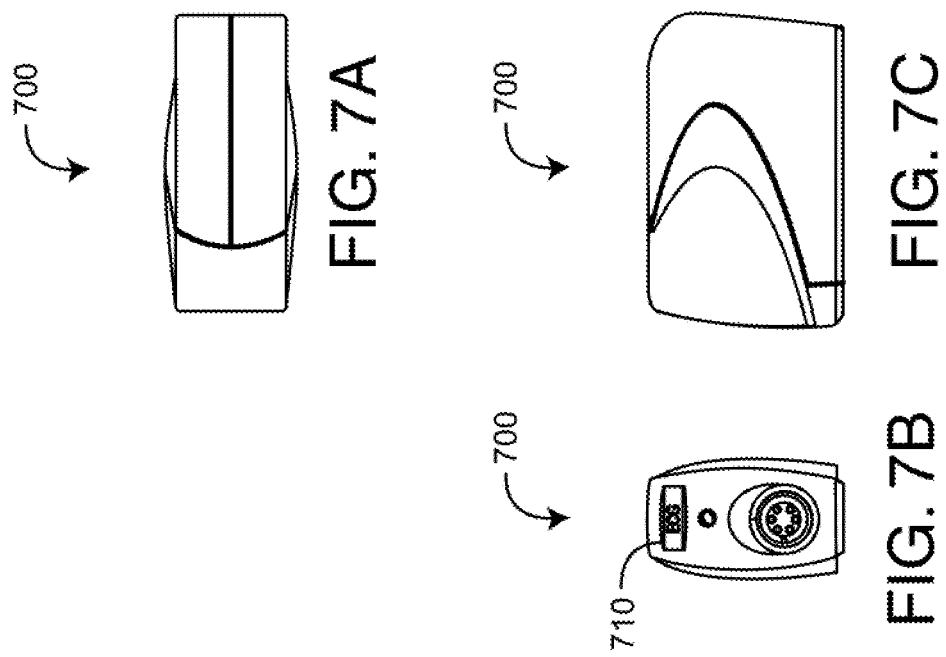

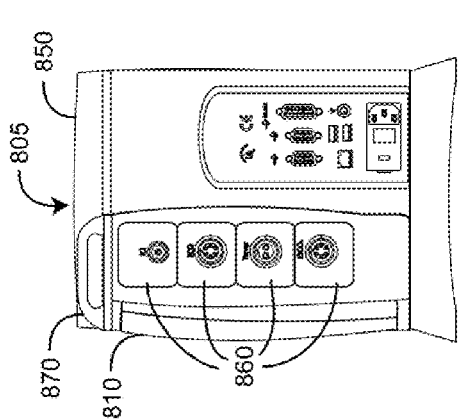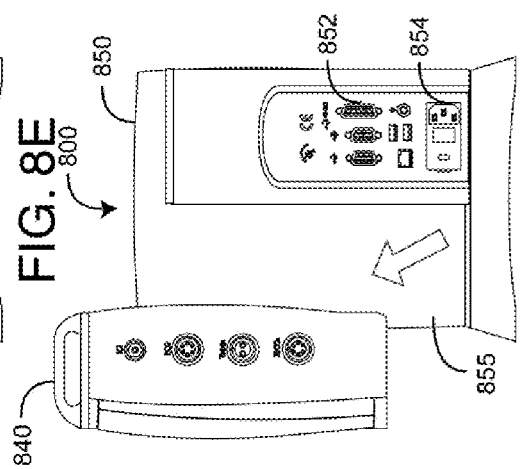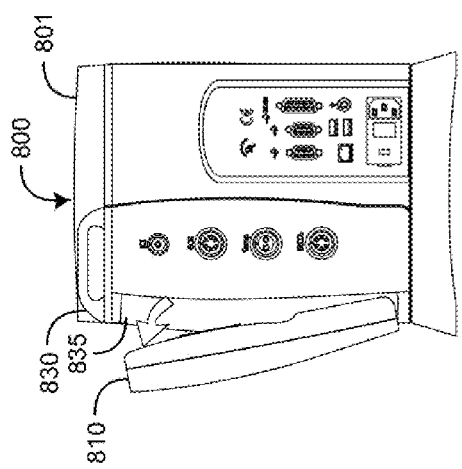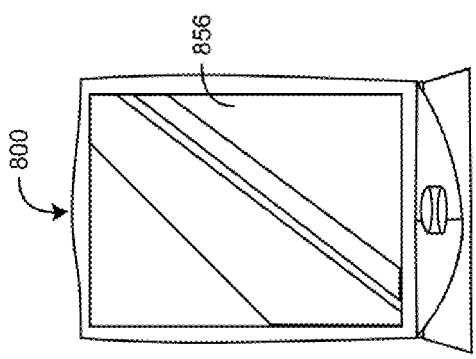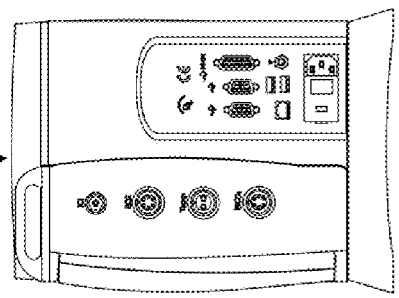

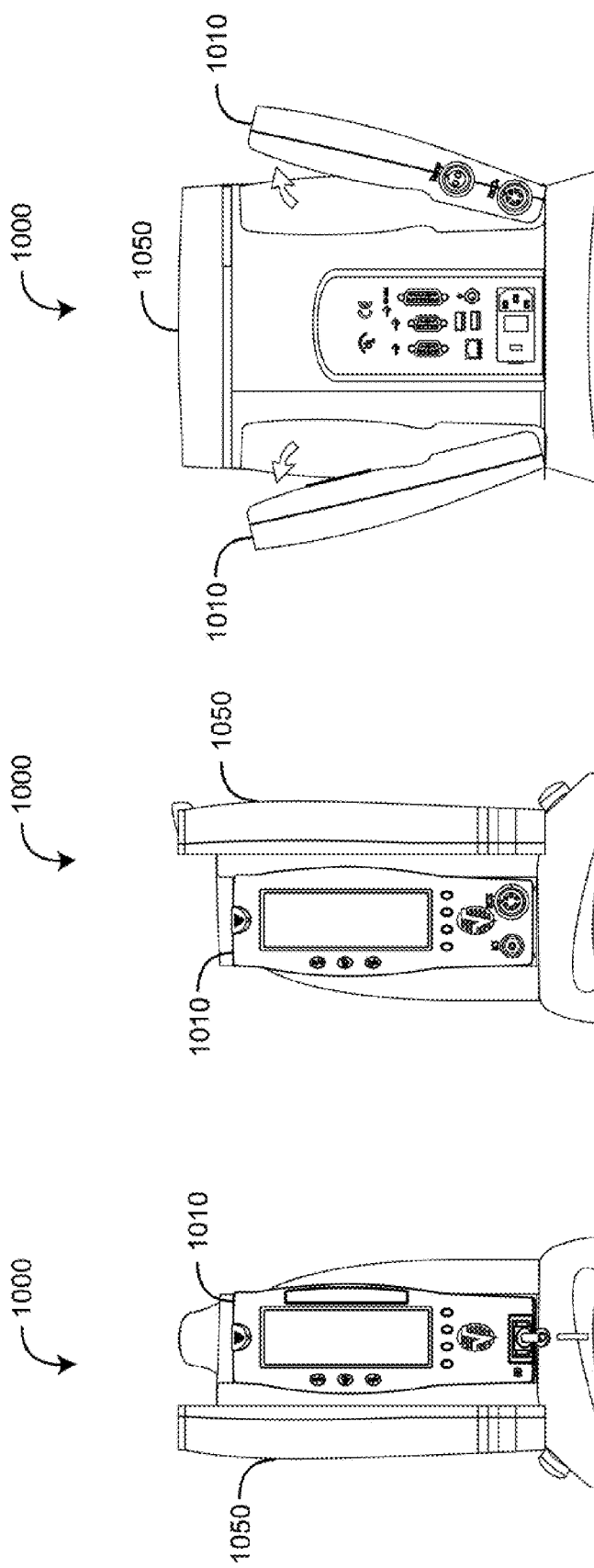

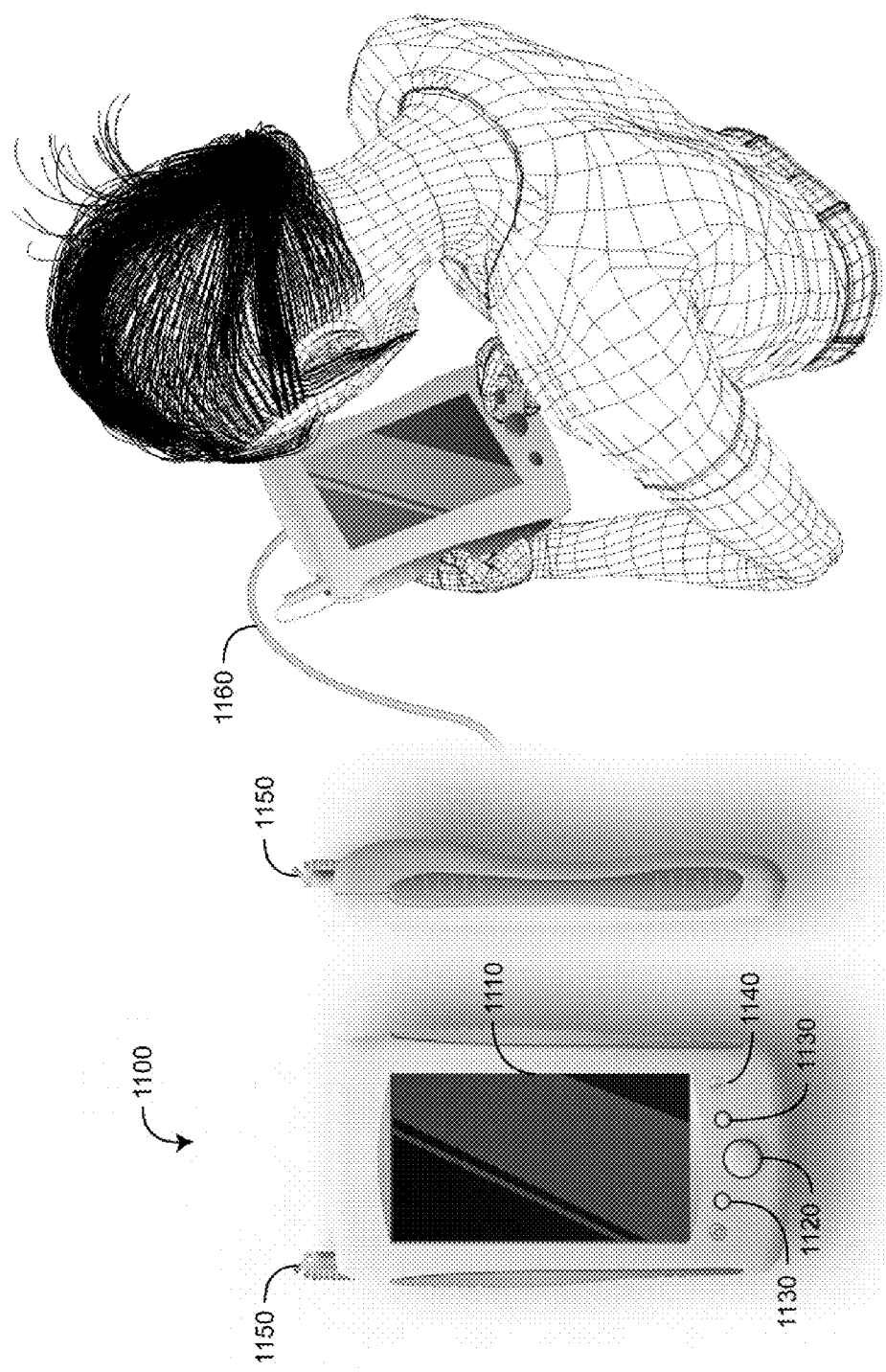

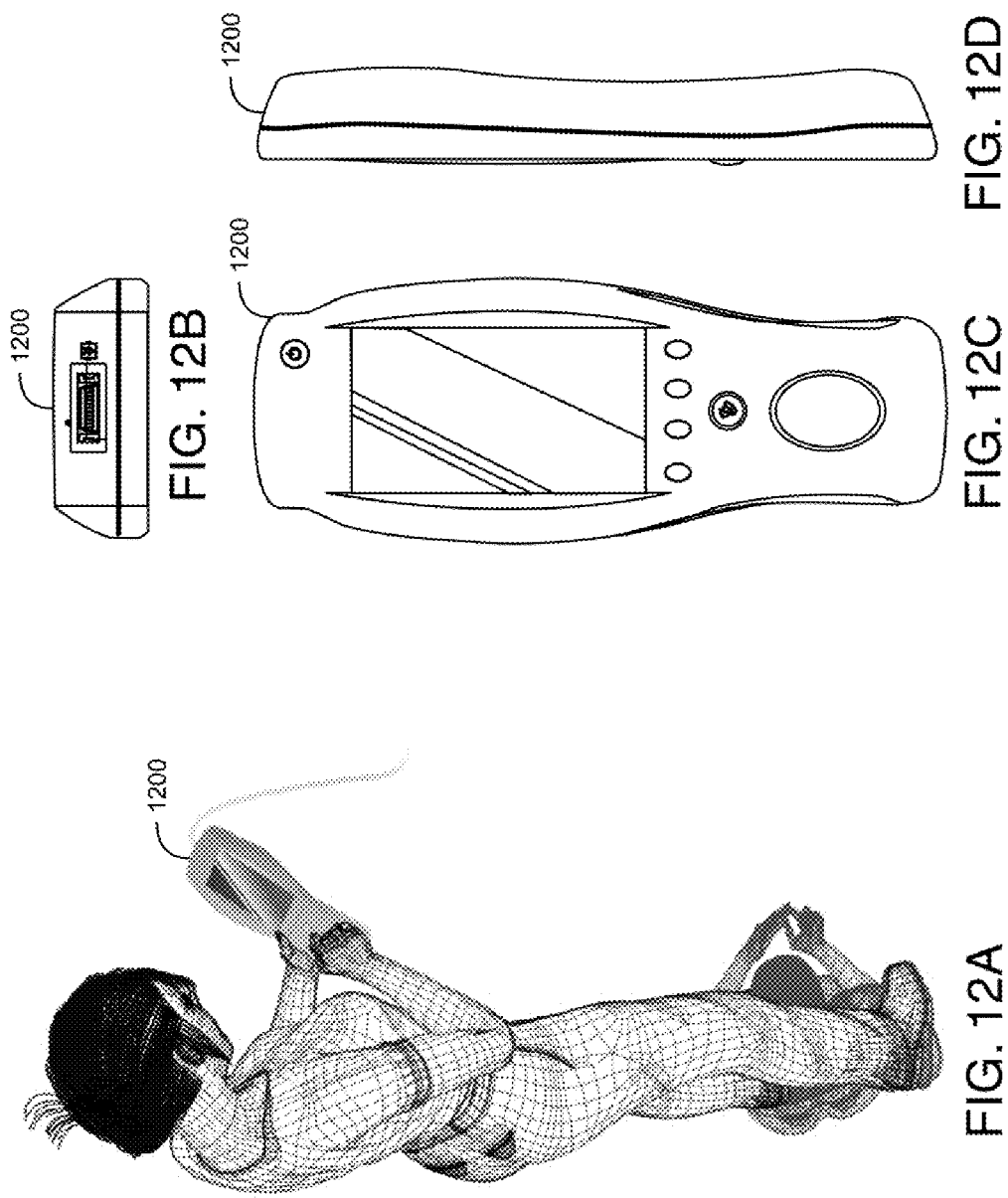

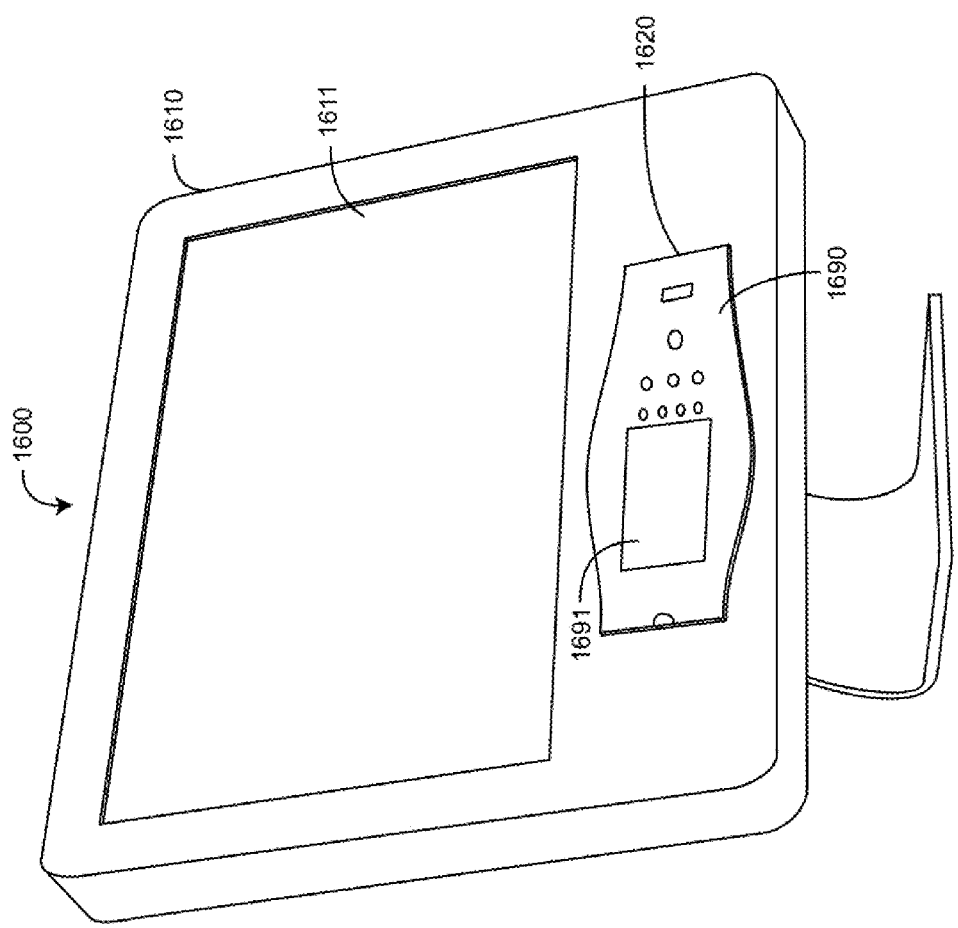

MODULAR PATIENT MONITOR

CROSS-REFERENCE TO RELATED APPLICATIONS

This application is a continuation-in-part of pending application Ser. No. 11/903,746, filed Sep. 24, 2007, entitled Modular Patient Monitor, which claims the benefit under 35 U.S.C. of §119(e) of U.S. Provisional Application No. 60/846,471, filed Sep. 22, 2006, entitled Modular Patient Monitor, the disclosures of which are hereby incorporated by reference in their entirety.

BACKGROUND OF THE INVENTION

Pulse oximetry is a widely accepted continuous and non-invasive method of measuring the level of arterial oxygen saturation in blood. A typical pulse oximetry system has a sensor, a patient monitor and a patient cable. The sensor is placed on a patient fleshy tissue site, usually on the fingertip for adults and the hand or foot for neonates and connected to the patient monitor via the patient cable. The sensor provides a sensor signal detected from the patient tissue site to the patient monitor. The patient monitor displays the calculated data as a percentage value for arterial oxygen saturation (SpO2), as a pulse rate (PR) and as a pulse waveform (plethysmograph or "pleth").

SUMMARY OF THE INVENTION

A modular patient monitor provides a multipurpose, scalable solution for various patient monitoring applications. In an embodiment, a modular patient monitor utilizes multiple wavelength optical sensor and acoustic sensor technologies to provide blood constituent monitoring and acoustic respiration monitoring (ARM) at its core, including pulse oximetry parameters and additional blood parameter measurements such as carboxyhemoglobin (HbCO) and methemoglobin (HbMet). Pulse oximetry monitors and sensors are described in U.S. Pat. No. 5,782,757 entitled Low-Noise Optical Probes and U.S. Pat. No. 5,632,272 entitled Signal Processing Apparatus, both incorporated by reference herein. Advanced blood parameter monitors and sensors providing blood parameter measurements in addition to pulse oximetry are described in U.S. patent application Ser. No. 11/367,013, filed Mar. 1, 2006 entitled Multiple Wavelength Sensor Emitters and U.S. patent application Ser. No. 11/367,014, filed Mar. 1, 2006 entitled Non-Invasive Multi-Parameter Monitor, both incorporated by reference herein. Acoustic respiration sensors and monitors are described in U.S. Pat. No. 6,661,161 entitled Piezoelectric Biological Sound Monitor with Printed Circuit Board and U.S. patent application Ser. No. 11/547,570 filed Jun. 19, 2007 entitled Non-Invasive Monitoring of Respiration Rate, Heart Rate and Apnea, both incorporated by reference herein.

Expansion modules provide blood pressure BP, blood glucose, ECG, CO2, depth of sedation and cerebral oximetry to name a few. The modular patient monitor is advantageously scalable in features and cost from a base unit to a high-end unit with the ability to measure multiple parameters from a variety of sensors. In an embodiment, the modular patient monitor incorporates advanced communication features that allow interfacing with other patient monitors and medical devices.

The modular patient monitor is adapted for use in hospital, sub-acute and general floor standalone, multi-parameter measurement applications by physicians, respiratory therapists, registered nurses and other trained clinical caregivers. It can be used in the hospital to interface with central monitoring and remote alarm systems. It also can be used to obtain routine vital signs and advanced diagnostic clinical information and as an in-house transport system with flexibility and portability for patient ambulation. Further uses for the modular patient monitor are clinical research and other data collection.

BRIEF DESCRIPTION OF THE DRAWINGS

FIGS. 1A-E are top, side, front, right and back views of a modular patient monitor;

FIGS. 5A-C are top, front and side views of a monitor cartridge;

FIGS. 6A-E are top, side, front, right and back views of another modular patient monitor embodiment having alternative cartridge embodiments;

FIGS. 7A-C are top, front and side views of an alternative cartridge embodiment;

FIGS. 8A-E are a front and various back views of yet another modular patient monitor embodiment having a shuttle, including a display and control; a docked shuttle; a docked shuttle with an undocked handheld; an undocked shuttle; and a shuttle having a handheld;

FIGS. 10A-C are side views and a back view, respectively, of an additional modular patient monitor embodiment having dual dockable handhelds;

FIGS. 11A-C are illustrations of a tablet-configured handheld monitor;

FIGS. 12A-D are front perspective, top, front and side views of an alternative handheld embodiment;

FIG. 16 is a perspective view of a flat panel display docking station;

DETAILED DESCRIPTION OF THE PREFERRED EMBODIMENTS

Figure 2A:
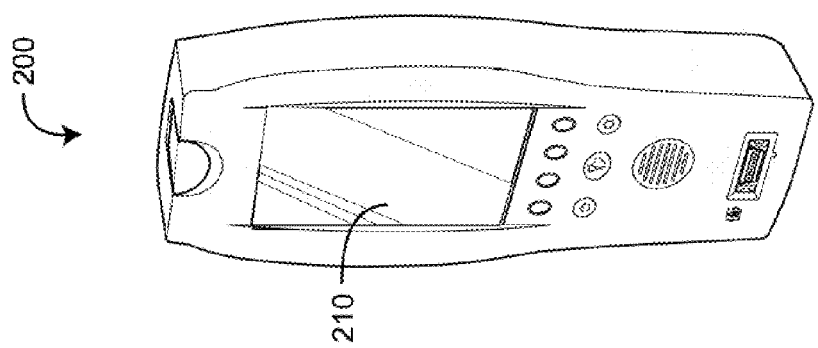
FIGS. 2A-B are front and perspective views of a handheld monitor.

FIGS. 1A-E illustrate a modular patient monitor embodiment 100 having a two-piece modular configuration, a handheld 200 unit and a configurable docking station 101. The handheld 200 docks into a handheld port 110 of the docking station 101, providing the modular patient monitor 100 with two-in-one functionality. In particular, the handheld 200 provides a specific set of clinically relevant parameters. The docking station 101 supports various parameters that are configured to specific hospital environments and/or patient populations including general floor, OR, ICU, ER, NICU, to name a few. Further, the docking station 101 has module ports 120 that accept plug-in expansion modules 500 for additional parameters and technologies. The handheld 200 docked into the docking station 101 allows access to all available parameters providing maximum connectivity, functionality and a larger color display 300. The modular patient monitor 100 provides standalone multi-parameter applications, and the handheld 200 is detachable to provide portability for patient ambulation and in-house transport.

As shown in FIGS. 1A-E, the docking station 101 has a dashboard 130, with a trim knob 140 and buttons 150 so as to support system navigation and data entry. The trim knob 140 is a primary means for system navigation and data entry with an option of a keyboard and mouse as a secondary means.

The docking station 101 also has a power supply module 160 and connectivity ports 170. The handheld 200 mechanically attaches to and electrically connects to the docking station 101 when docked, such that the two devices function as one unit and both the handheld display 210 and the docking station display 300 provide user information. In an embodiment, the handheld 200 docks on a docking station side such that the handheld display 210 is visible from that side of the docking station 101 (FIG. 10). In addition, the docking station 101 has one or more module slots 120 that accommodate external modules 400, as described with respect to FIGS. 5A-C, below.

Also shown in FIGS. 1A-E, controls of the docking station 101 take precedence over those of the handheld 200 when docked. However, the handheld buttons 220 also work for back up purposes. In an embodiment, buttons 150, 220 on the docking station dashboard 130 and on the handheld 200 provide for alarm suspend/silence and mode/enter. The trim knob 140 is the primary method to toggle thru screen menus on the dashboard 130. The procedure includes next, up, down or across page navigation, parameter selection and entry, data entry, alarm limit selection and selection of probe-off detection sensitivity. As a secondary control method, the modular patient monitor 100 has a port for an external keyboard for patient context entry and to navigate the menu. In an embodiment, the docking station 150 has a touch screen. In an embodiment, the modular patient monitor 100 has a bar code scanner module adapted to automatically enter patient context data.

The modular patient monitor 100 includes an integral handle for ease of carrying and dead space for storage for items such as sensors, reusable cables, ICI cable and cuff, $EtCO_2$ hardware and tubing, temperature disposables, acoustic respiratory sensors, power cords and other accessories such as ECG leads, BP cuffs, temperature probes and respiration tapes to name a few. The monitor 100 can operate on AC power or battery power. The modular patient monitor 100 stands upright on a flat surface and allows for flexible mounting such as to an anesthesia machine, bedside table and computer on wheels.

Figure 2B:
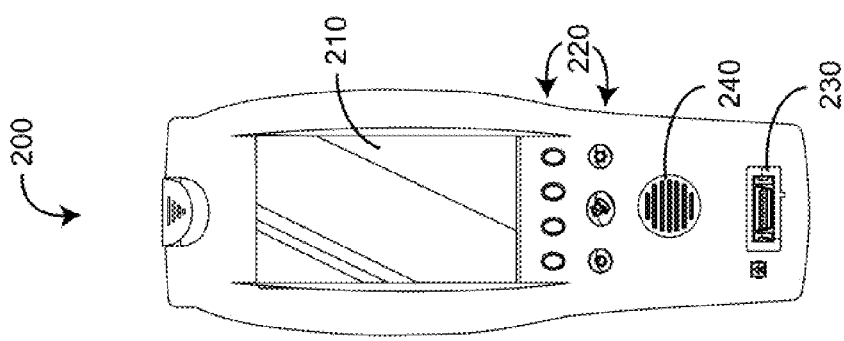

FIGS. 2A-B illustrate a handheld monitor 200, which provides pulse oximetry parameters including oxygen saturation ($SpO_2$), pulse rate (PR), perfusion index (PI), signal quality (SiQ) and a pulse waveform (pleth), among others. In an embodiment, the handheld 200 also provides measurements of other blood constituent parameters that can be derived from a multiple wavelength optical sensor, such as carboxyhemoglobin (HbCO) and methemoglobin (HbMet). The handheld 200 has a color display 210, user interface buttons 220, an optical sensor port 230 and speaker 240. The handheld 200 also has external I/O such as a bar code reader and bedside printer connectivity. The handheld 200 also has a flexible architecture, power and memory headroom to display additional parameters, such as $Sp_vO_2$, blood glucose, lactate to name a few, derived from other noninvasive sensors such as acoustic, fetal oximetry, blood pressure and ECG sensors to name a few. In an embodiment, the handheld unit 200 has an active matrix (TFT) color display 210, an optional wireless module, an optional interactive touch-screen with on-screen keyboard and a high quality audio system. In another embodiment, the handheld 200 is a Radical® or Radical-7™ available from Masimo Corporation, Irvine Calif., which provides Masimo SET® and Masimo Rainbow™ parameters. A color LCD screen handheld user interface is described in U.S. Provisional Patent Application No. 60/846,472 titled Patient Monitor or User Interface, filed Sep. 22, 2006 and U.S. application Ser. No. 11/904,046 titled Patient Monitor User Interface, filed Sep. 24, 2007, both applications incorporated by reference herein.

Figure 3:
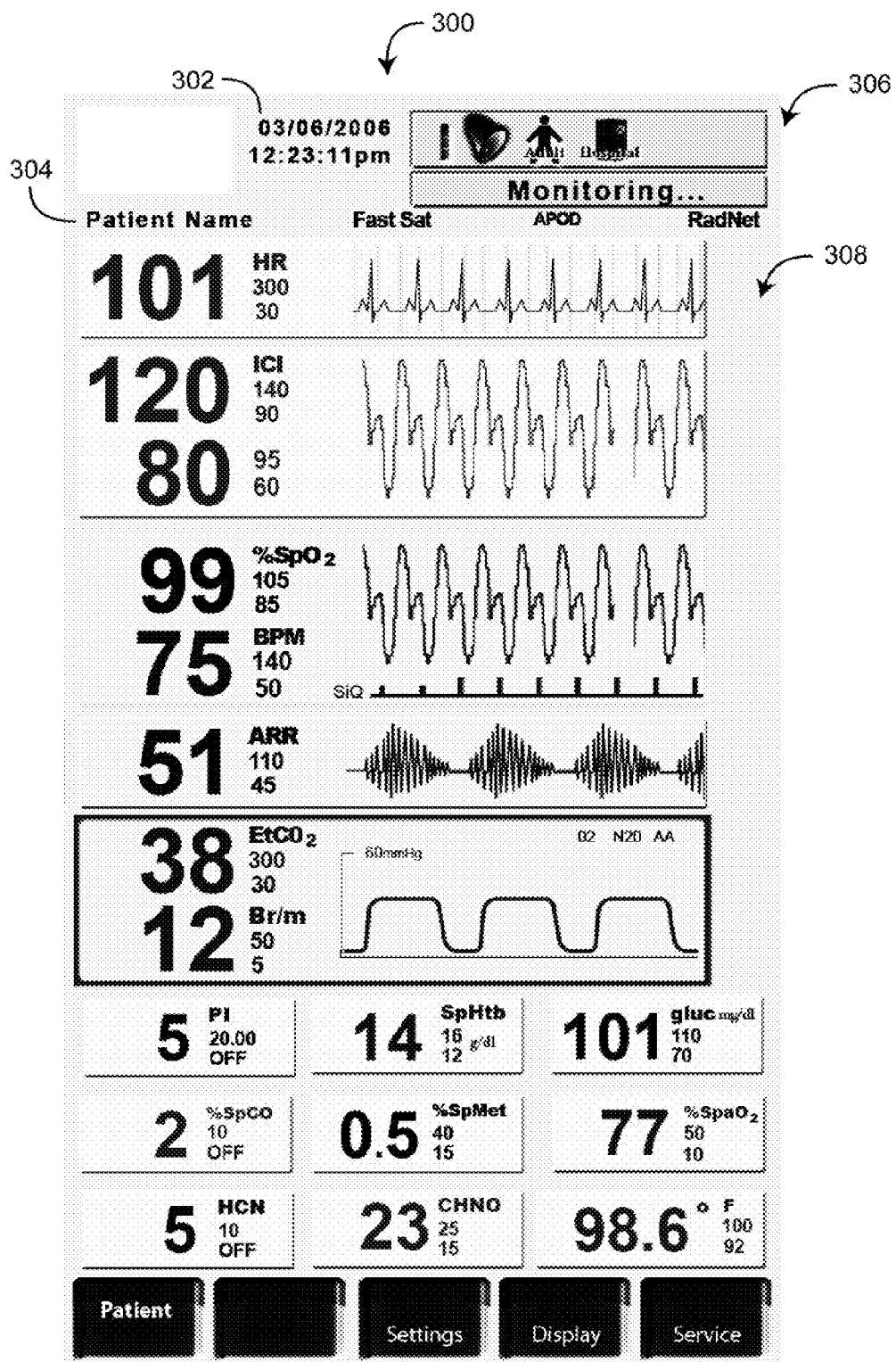
FIG. 3 is a docking station multiple parameter display.

FIG. 3 illustrates a modular patient monitor color display 300. The modular patient monitor display 300 auto-scales its presentation of parameter information based upon the parameters that are active. Fewer parameters result in the display 300 of larger digits and more waveform cycles. In an embodiment, the display 300 has a main menu screen showing date and time 302, patient data 304, battery life and alarm indicators 306 and all enabled parameters 308. Date and time 302 can be enabled or disabled. The display 300 may also have dynamic bar graphs or indicators to show perfusion index and signal quality. Waveforms are displayed for $SpO_2$, NIBP (non-invasive blood pressure), $EtCO_2$ (end-tidal carbon dioxide) and ECG (electrocardiogram) if enabled. Trend waveforms are displayed for parameters that are less dynamic, such as HbCO and HbMet. Further, the display 300 has individual text displays for alarms, alarm suspend, sensor off or no sensor, battery condition, sensitivity, trauma mode, AC power, printer function, recording function, connectivity messages and menus to name a few. Pulse search is indicated by blinking dashes in the pulse and parameter displays. In an embodiment, the color display 300 is an 11.1" LCD with allowance for the use of a 10.4" LCD within the standard mechanical design for the 11.1" display. The docking station 101 also supports any external VGA display.

An exemplar color print illustration of the color display 300 is disclosed in U.S. Provisional Application No. 60/846, 471 entitled Modular Patient Monitor, cited above. In particular, each of the displayed parameters are variously presented in one of a off-white to white shade, lime green to green shade, crimson to red shade, generally turquoise shade, generally chartreuse shade, yellow to gold shade, generally blue and generally purple shade, to name a few.

Figure 4:
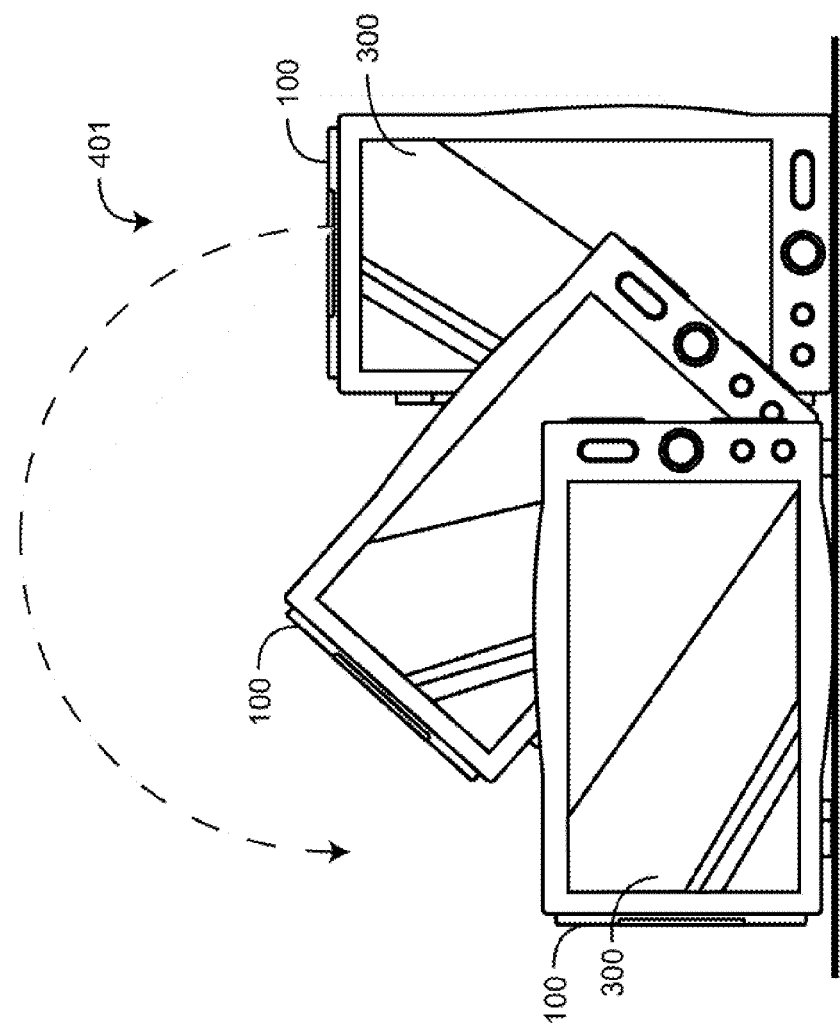
FIG. 4 is an illustration of a modular patient monitor having 90 degree rotation with corresponding display rotation.

FIG. 4 illustrates a modular patient monitor 100 having a vertical orientation 401 and a horizontal orientation 403. In the vertical orientation 401, the display 300 presents data in a vertical format, such as shown in FIG. 3, above. In the horizontal orientation 403, the display 300 presents data in a horizontal format, so that the data appears upright with respect to the viewer. That is, the display 300 automatically switches format according to the patient monitor 100 orientation. A patient monitor having a rotatable display format is described in U.S. Pat. No. 6,770,028 entitled Dual Mode Pulse Oximeter and incorporated by reference herein.

FIGS. 5A-C illustrate an expansion module 500, which the docking station 101 (FIGS. 1A-E) accepts for additional parameters and technologies, such as ICI-NIBP, glucose monitoring, ECG, EtCO$_2$, conscious sedation monitoring, cerebral oximetry, anesthetic agent monitoring, lactate, patient body temperature and assay cartridges, to name a few. The expansion module 500 has an indicator 510 indicating parameters to be provided. In one embodiment, the expansion module 500 provides two parameters to the docking station, which is adapted to accept two modules 500 for four additional parameters. In an embodiment, an ECG module is used to provide an R-wave trigger for ICI-NIBP.

As shown in FIGS. 1A-E, the modular patient monitor 100 includes various connectivity ports 170 such as Ethernet, USB, RS-232, RS-423, nurse call, external VGA and I/O ports for a keyboard and a bar code reader to name a few. As an option, the modular patient monitor 100 has on-board and bedside recorder capability. The modular patient monitor 100 also supports multiple wireless and hardwired communication platforms, web server technology that allows remote viewing of data as well as limited bi-directional control of module functionality and an optional wireless connectivity standards base technology, such as IEEE 802.11x. The wireless option is provided in the handheld 200 and the docking station 101. A wireless module supports the downloading and temporary storage of upgrade software from a remote central server to a destination docking station or a specific module. In an embodiment, the modular patient monitor 100 supports patient context management, specifically the ability to upload or alternatively enter patient unique identification. The modular patient monitor 100 also connects both wired and wirelessly to other patient monitors.

The modular patient monitor 100 may be logged onto via the Internet so as to download raw waveforms and stored trending data for both customer service purposes and for data mining to enhance algorithms and so as to be uploaded with firmware updates. The modular patient monitor 100 may also incorporate removable storage media for the same purpose. In an embodiment, removable storage media functions as a black box, which is a diagnostic tool to retrieve device use information. In particular, the black box can record values displayed, raw waveforms including sounds, and buttons touched by the end user. A patient monitor with removable storage media is described in U.S. patent Ser. No. 10/983,048 entitled Pulse Oximetry Data Capture System filed Nov. 5, 2004 and incorporated by reference herein.

The modular patient monitor 100 may also have an audio module slot (not shown) accommodating an external audio system and wireless headphone module. In an embodiment, the docking station 101 audio system is configured to reproduce respiratory sounds from an ARR (acoustic respiratory rate) sensor.

In an embodiment, the modular patient monitor 100 has a redundant speaker system for alarms. The modular patient monitor 100 may also include alarms for all parameters and a parameter fusion alarm that involves analysis of multiple parameters in parallel. A user can select custom default alarm parameters for adult, pediatric and neonatal patients. A patient monitor having redundant alarm speakers is described in U.S. patent application Ser. No. 11/546,927 entitled Robust Alarm System, filed Oct. 12, 2006 and incorporated by reference herein.

An alarm condition exists for low battery, sensor-off patient, defective sensor, ambient light, parameter limit exceeded and defective speakers, as examples. Audible alarm volume is adjustable and when muted, a visual indicator is illuminated. In an embodiment, the volume is adjustable in at least of four discrete steps. The parameter display flashes to indicate which values are exceeding alarm limits, the parameter is enlarged automatically, and numerics are displayed in either RED or with a RED background. The audible alarm is silence-able with a default alarm silence period for up to two minutes. This delay can be user configurable. Separate from sleep mode, the audible alarms are permanently mutable via a password-protected sub-menu. The visual alarm indicator still flashes to indicate an alarm condition. A visual indicator on the dashboard indicates an alarm silence condition, such as blinking for temporary silence and solid for muted. An alarm speaker is mounted so as not to be susceptible to muffling from a bed surface, attached external monitor surface or other type of flat resting surface. Redundant and smart alarm annunciation is also provided.

The user accesses the setup menu via a front dashboard knob 140 and mode/enter button 150. TABLE 1 shows user settable parameters. The user can override default settings on a patient-by-patient basis via setup menus.

TABLE 1

| PARAMETER SETTINGS |
| --- |
| SpO$_2$ high & low limit |
| Pulse Rate high & low limit |
| Pulse Tone volume |
| MetHb high and low limit |
| HbCO high & low limit |
| ICI high and low limit |
| tHb high and low limit |
| EtCO$_2$ high and low limit |
| ARR high and low limit |
| Temp high and low limit |
| Glucose high and low limit |
| Audible alarm volume |

Default settings are stored in non-volatile memory (NVM). There is a factory, hospital and user default setting which may be automatically based on patient recognition. The user can choose any of the three at any time. The user may over-write hospital and user default settings with their own preferences via a password protected "save as default" setup menu function. All parameters return to hospital default settings after a power cycle.

In one embodiment, the default settings are as shown in TABLE 2, stored in NVM. These settings are also overwritten into NVM as a result of a factory reset or return to factory defaults function from within the setup menus.

TABLE 2

| PARAMETER | FACTORY DEFAULT |
| --- | --- |
| SpO$_2$ high limit | Off |
| SpO$_2$ low limit | 90 |
| Pulse Rate high limit | 140 |
| Pulse Rate low limit | 40 |
| Alarm Volume | 2 (of 4) |
| Pulse tone volume | 2 (of 4) |
| MetHb high limit | 5% |
| MetHb low limit | Off |
| HbCO high limit | 10% |
| HbCO low limit | Off |
| LCD brightness | 3 (of 5) |

FIGS. 6A-E illustrate another modular patient monitor 600 embodiment having a docking station 601, a handheld monitor 602 and parameter cartridges 700. Each cartridge 700 provides one parameter to the docking station 601, which accepts four cartridges 700 for a total of four additional parameters. Further, the patient monitor 600 also has a cord management channel 630, an oral temperature probe 660 and probe covers 670 located on the docking station 601. The docking station 601 has a trim knob 652 and control buttons 654 on a front stand 653 so as to support system navigation and data entry. The docking station 601 also has a color display 605, a thermal printer 620, an alarm indicator light bar 651, a thermal printer paper door 657 and a handle 659, a sensor holder 655, connectivity ports 680 and a power supply module 690. FIGS. 7A-C illustrate a parameter cartridge 700 having an indicator 710 indicating the parameter or technology provided.

FIGS. 8A-D illustrate a three-piece modular patient monitor 800 including a handheld monitor 810, a shuttle station 830 and a docking station 850. The docking station 850 has a shuttle port 855 that allows the shuttle station 830 to dock. The shuttle station 830 has a handheld port 835 that allows the handheld monitor 810 to dock. Accordingly, the modular patient monitor 800 has three-in-one functionality including a handheld 810, a handheld 810 docked into a shuttle station 830 as a handheld/shuttle 840 and a handheld/shuttle 840 docked into a docking station 850. When docked, the three modules of handheld 810, shuttle 830 and docking station 850 function as one unit.

As shown in FIGS. 8A-D, the handheld module 810 functions independently from the shuttle 830 and docking station 850 and is used as an ultra-light weight transport device with its own battery power. The handheld 810 docked into the shuttle module 830 functions independently of the docking station 850 and expands the handheld parameter capability to the ability to measure all parameters available. The docking station 850, in turn, provides the shuttle 830 or handheld/shuttle 840 with connectivity ports 852, a power supply module 854, a large color display 856, wireless and hardwired communications platforms, a web server and an optional printer. As such, the docking station 850 charges the handheld 810 and shuttle 830, provides a larger screen and controls, such as a trim knob, allows wireless, hardwired and Internet communications and provides connectivity to various external devices. FIG. 8E illustrates another modular patient monitor embodiment 805 having a shuttle 870 with plug-in modules 860 for expanded parameter functionality.

In an embodiment, the handheld monitor 810 incorporates blood parameter measurement technologies including HbCO, HbMet, $SpO_2$ and Hbt, and the shuttle station 830 incorporates non-blood parameters, such as intelligent cuff inflation (ICI), end-tidal $CO_2$ ($EtCO_2$), acoustic respiration rate (ARR), patient body temperature (Temp) and ECG, to name a few. In an alternative embodiment, parameters such as $SpO_2$, ARR and ECG that clinicians need during in-house transports or patient ambulation are loaded into the handheld 810.

Figure 9:
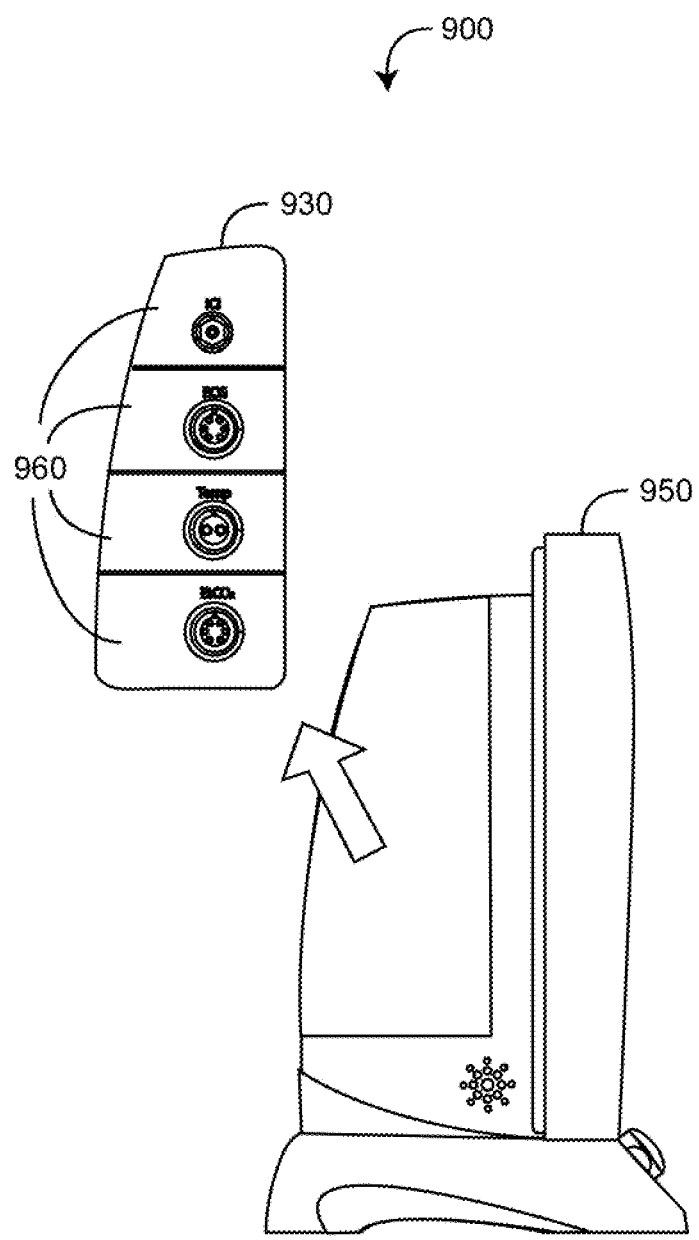
FIG. 9 is a modular patient monitor side view of a further modular patient monitor embodiment having a shuttle without a docking handheld.

FIG. 9 illustrates a two-piece modular patient monitor 900 having a shuttle 930 and a docking station 950 without a corresponding handheld. In an embodiment, the shuttle 930 has plug-in modules 960 for added parameter functions.

FIGS. 10A-C illustrate yet another modular patient monitor 1000 embodiment having dual removable handhelds 1010 and a docking station 1050 without a corresponding shuttle. For example, the handhelds 1010 may include one blood parameter monitor and one non-blood parameter monitor.

Figure 13B:
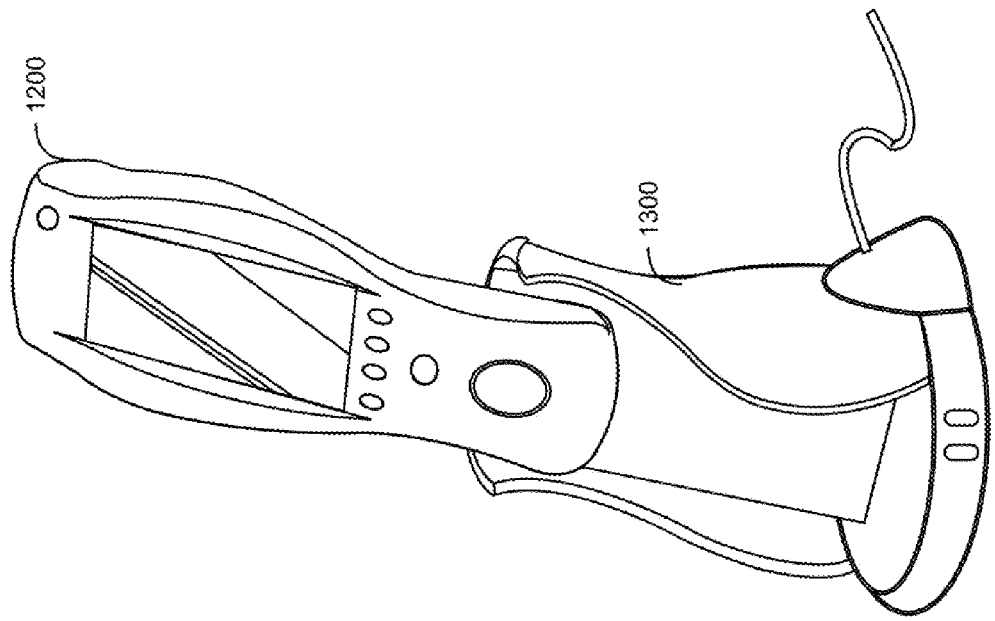
FIGS. 13A-B are front perspective views of an alternative handheld embodiment plugged into, and removed from, a charger.
Figure 13A:
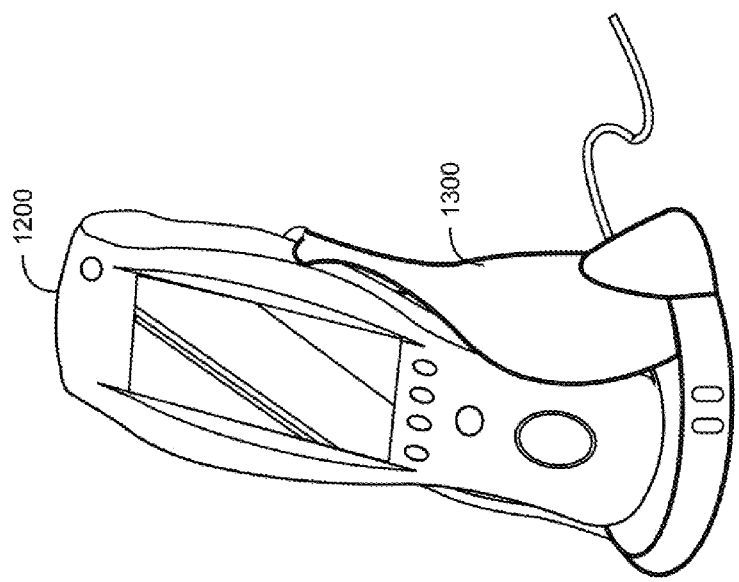

FIGS. 11A-C illustrate a handheld tablet monitor 1100 having a display 1110, a trim knob 1120 and control buttons 1130. An electroluminescent lamp 1140 on the front panel provides a thin uniform lighting with low power consumption. A temperature probe 1150 is attached to the monitor 1100. The tablet monitor 1100 connects to a multiple parameter sensor through a patient cable 1160. FIGS. 12-13 illustrate a handheld monitor 1200 configured to plug into a compact holder/battery charger 1300. The handheld monitor 1200 is adapted to plug into the compact charger 1300.

Figure 14:
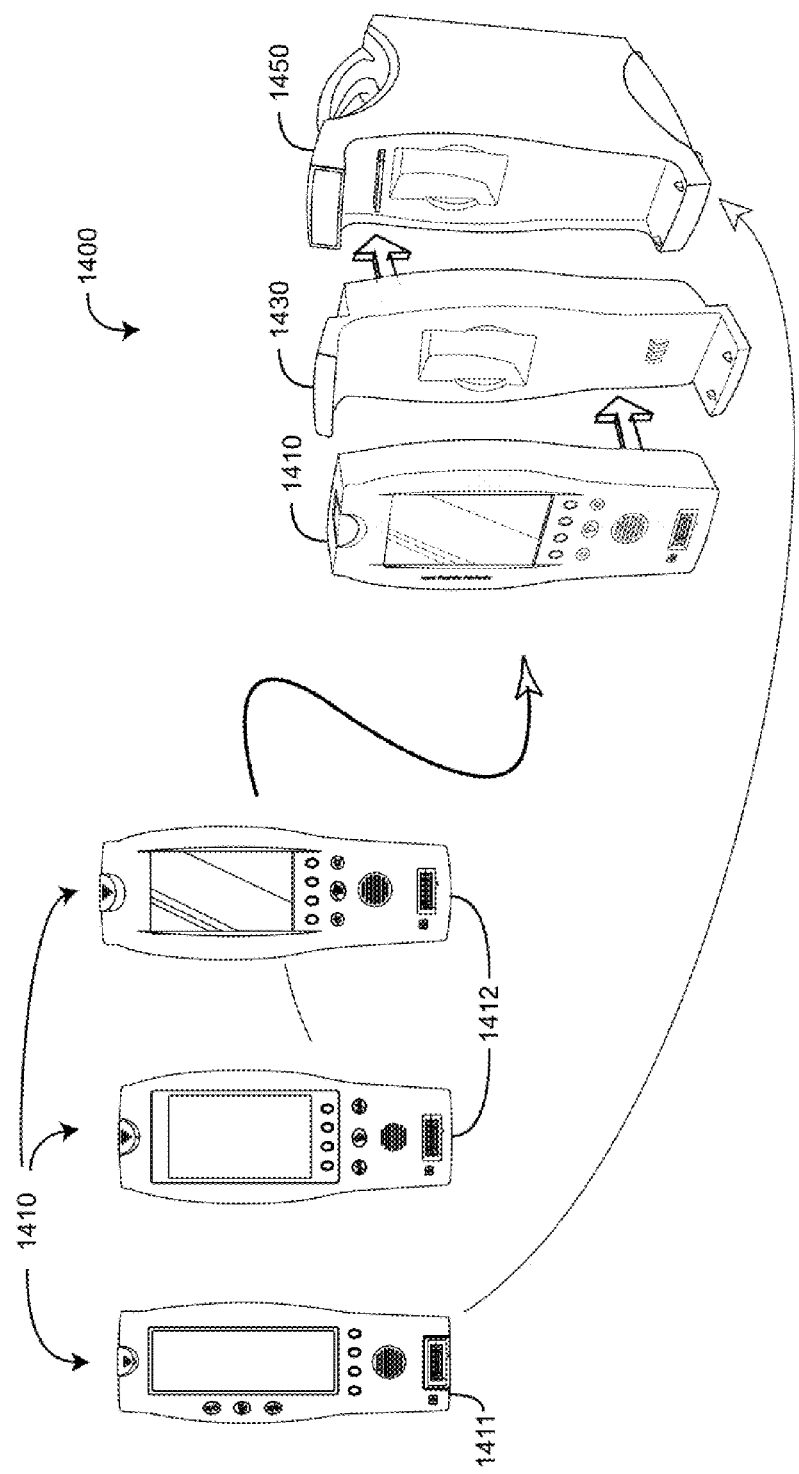
FIG. 14 is a perspective view of upgrade and legacy handhelds installable into a legacy docking station directly or via a docking station adapter.

FIG. 14 illustrates a modular patient monitor 1400 embodiment having various handheld monitors 1410, a docking station adapter 1430 and a legacy docking station 1450. The handheld monitors 1410 can include legacy handhelds 1411 and upgrade handhelds 1412. The docking station adapter 1430 is configured for the legacy docking station 1450 so that both legacy handhelds 1411 and upgrade handhelds 1412 can dock into the legacy docking station 1450 directly or via the docking station adapter 1430.

Figure 15A:
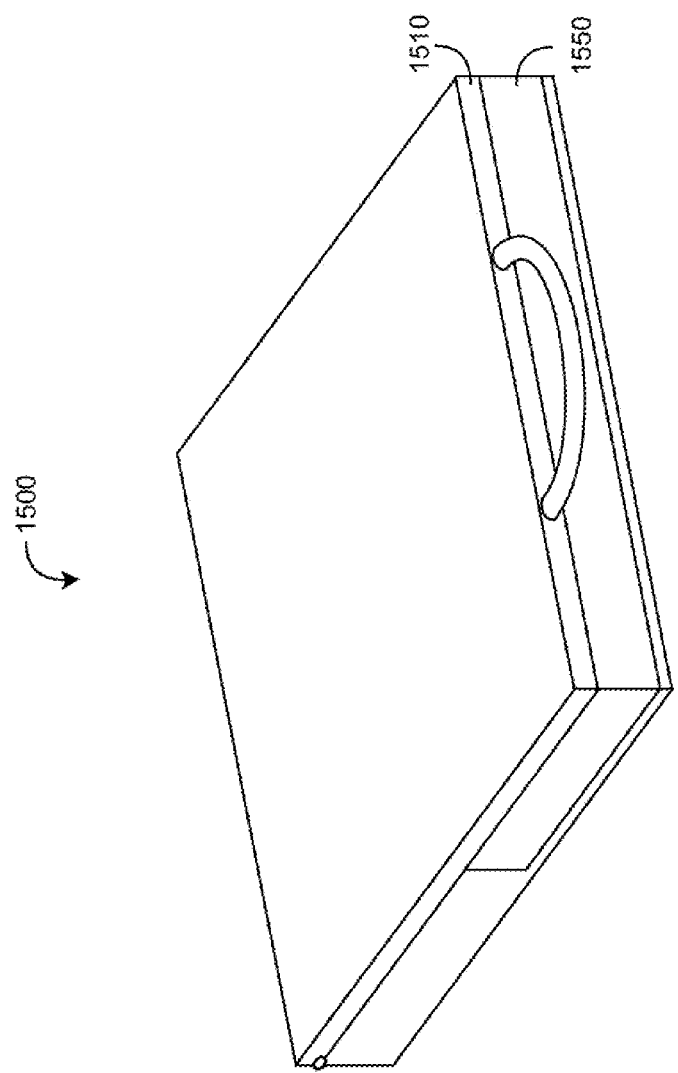
FIGS. 15A-B are closed and opened views, respectively, of a notebook-style modular patient monitor embodiment having a foldable display.
Figure 15B:
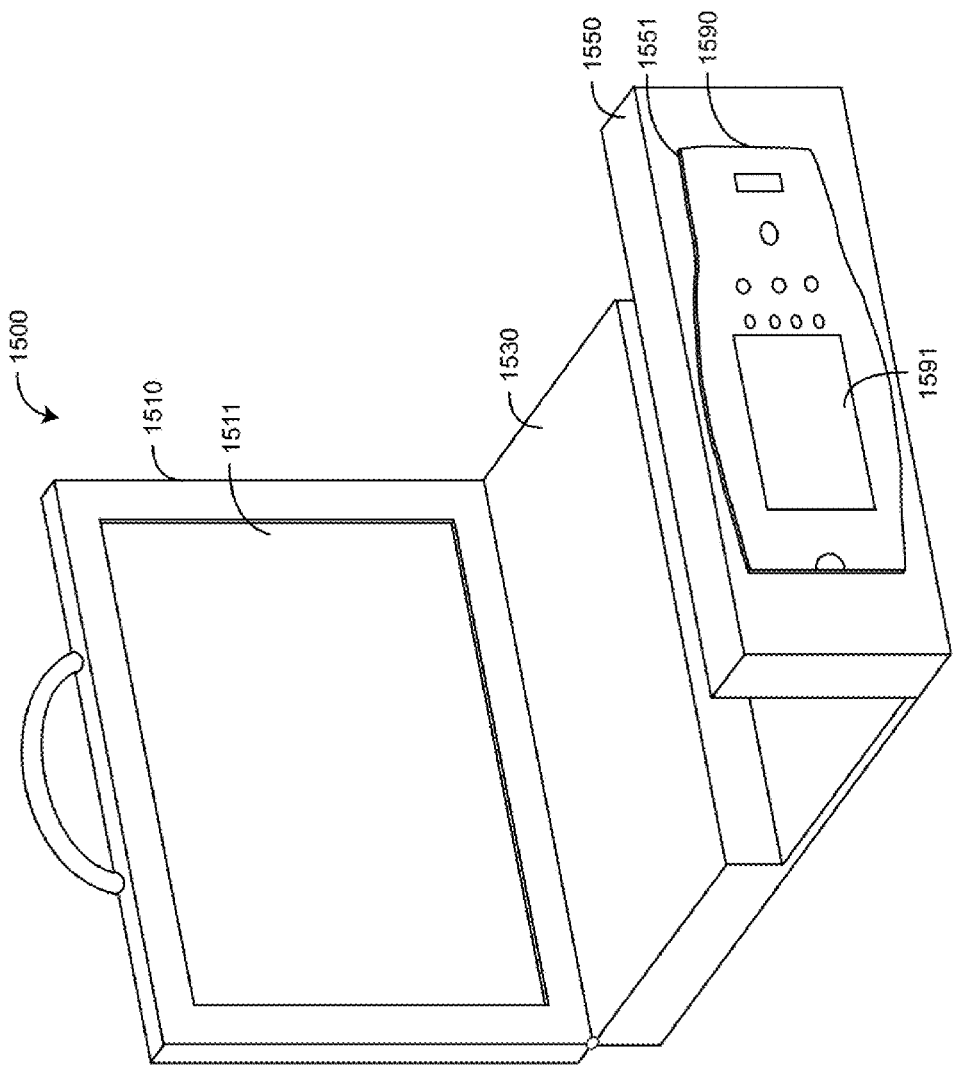

FIGS. 15A-B illustrate a "notebook" modular patient monitor 1500 embodiment having a foldable lid 1510, a fixed body 1530 and a foldable docking station 1550. The fixed body 1530 houses patient monitor electronics and provides external device connectivity at a back end (not visible). The lid 1510 has a notebook display 1511, such as a color LCD. The docking station 1550 has a port 1551 that removably connects, both mechanically and electrically, a corresponding handheld monitor 1590, such as the handheld embodiments described above. In a closed position (FIG. 15A), the notebook monitor 1500 can be carried via an optional handle or simply in hand or under an arm. In an open position (FIG. 15B), the notebook monitor is operational, connecting to patient sensors via the handheld 1590 or a sensor connector (not shown) on the back end of the notebook. In the open position, the docking station 1550 can stay in a stowed or folded position (not shown) so that the handheld screen 1591 faces upward. Alternatively, in the open position, the docking station 1550 is unfolded as shown (FIG. 15B) so that the handheld display 1591 can be easily viewed from the front of the notebook in conjunction with the notebook display 1511 in the lid 1510. In an embodiment, the notebook 1500 can have a conventional keyboard and touch pad, have conventional monitor controls, incorporate a conventional computer and peripherals or a combination of the above. As shown, the notebook display 1511 faces inward, so that the display 1511 is protected in the folded position. In another embodiment, the display 1511 faces outward (not shown).

FIG. 16 illustrates a flat panel modular patient monitor embodiment 1600 having a flat panel body 1610 housing a flat panel display 1611 and a handheld port 1620. The handheld port 1620 removably accepts a handheld monitor 1690 having a handheld display 1691, such as the handheld monitors described above. The flat panel monitor 1600 can be free-standing on a table top, wall-mounted or mounted on or integrated within a patient bed, as a few examples. The flat panel monitor 1600 can be simply a docking and display device or can provide built-in patient monitoring functions and parameters not available to the handheld 1690.

Figure 17:
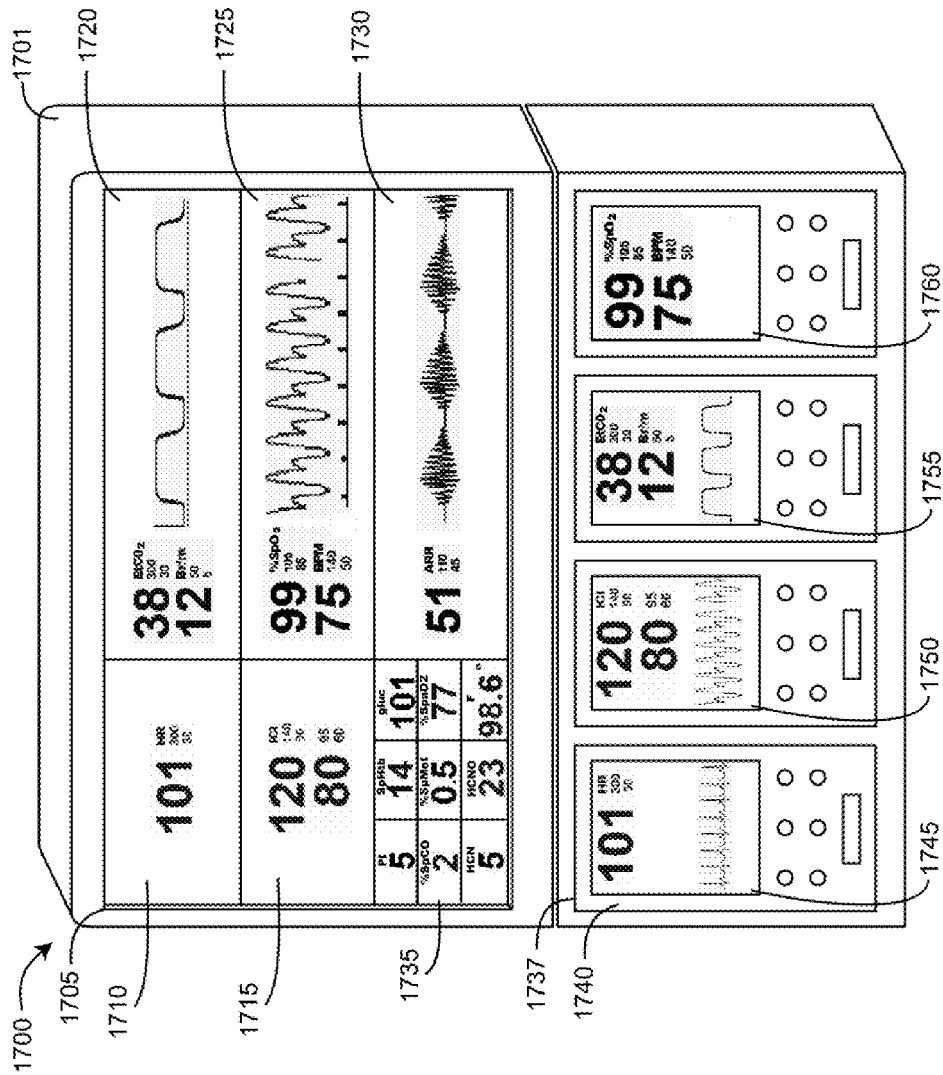
FIG. 17 illustrates a perspective view of a modular patient monitor embodiment having a docking station for handheld monitors.

FIG. 17 illustrates a perspective view of a modular patient monitor 1700 embodiment having a docking station 1701 for handheld or portable monitors. The docking station includes a display 1705 for displaying one or more physiological parameters 1710, 1715, 1720, 1725, 1730, 1735. The docking station further includes one or more docking ports 1737 for receiving one or more handheld monitors 1740 having a display. In the illustrated embodiment, the modular patient monitor includes four docking ports integrated into the docking station for receiving handheld monitors. In some embodiments, the docking ports can be positioned on the docking station such that the docking station display and the handheld monitor displays are viewable at the same time. Typically, the docking station display will be several times larger than a handheld monitor display. Measurements of a physiological parameter can be spanned across the docking station display and the handheld monitor displays 1745, 1750, 1755, 1760.

In some embodiments, the display 1705 or additional displays can be physically separate from the docking station 1701. In such embodiments, the separate display is in communication with the docking station, either wirelessly or through a wire. In one embodiment, multiple displays can be in communication with the docking station simultaneously, allowing measurements of physical parameters to be spanned across multiple docking station displays and multiple handheld monitors.

In one embodiment, the docking station 1701 can have its own stand-alone patient monitoring functionality, such as for pulse oximetry, and can operate without an attached handheld monitor. The docking station receives patient data and determines measurements to display for a monitored physiological parameter.

One or more of handheld monitors 1740 can be docked to the docking station 1701. A handheld monitor 1740 can operate independently of the docking station. In some embodiments, a particular handheld monitor can be configured to receive patient data and determine measurement to display for a particular physiological parameter, such as, for example, blood pressure, other blood parameters, ECG, and/or respiration. In one embodiment, the handheld monitor can operate as a portable monitor, particularly where only some parameters need to be measured. For example, the handheld monitor, while providing patient monitoring, can travel with a patient being moved from one hospital room to another or can be used with a patient travelling by ambulance. Once the patient reaches his destination, the handheld monitor can be docked to a docking station at the destination for expanded monitoring.

In some embodiments, when a handheld monitor 1740 is docked to the docking station 1701, additional parameters can become available for display on the docking station display 1705. The docking station 1701 can auto-scale existing measurements on the display to make room for measurements of the additional parameters. In one embodiment, a user can select which measurements to display, drop, and/or span using the controls on the patient monitor 1700. In some embodiments, the patient monitor can have an algorithm for selecting measurements to display, drop, and/or span, such as by ranking of measurements, display templates, and/or settings. In one embodiment, the additional parameters can be removed from the docking station display when the handheld monitor associated with the parameters is undocked from the docking station.

In order to expand display space on the docking station display 1705, measurements can be spanned across the docking station display 1705 and the handheld monitor displays 1745, 1750, 1755, 1760. In one embodiment, the measurements can be spanned by displaying a partial set of the measurements on the docking station and additional measurements on the portable monitor. For example, portions of the docking station display 1710, 1715 can show some measurements of a parameter, such as a numerical value, while the handheld monitor display 1745, 1750 shows additional measurements, such as the numerical value and an associated waveform. By keeping the additional measurements on a particular handheld monitor, such as heart rate waveform on a heart monitor, the measurements can be more easily recognizable to a caregiver, increasing monitoring efficiency and expanding the display area.

Alternatively, measurements can be spanned by mirroring on the docking station display 1705 a handheld monitor display. For example, portions of the docking station display 1720 can display all the measurements on a handheld monitor display 1755, such as a numerical value and a waveform.

In one embodiment, the spanning feature can take advantage of the docking station display's 1705 greater size relative to the handheld monitor displays to display additional measurements and/or to display a measurement in greater detail. For example, portions of the docking display 1725 can display numerical values and a waveform while a handheld monitor display 1760 shows only a numerical value. In another example, the docking station can display a waveform measured over a longer time period than a waveform displayed on the handheld monitor, providing greater detail.

In some embodiments, the portable monitor 1740 displays a set of measurements when operating independently (e.g. a numerical value and a waveform), but only a partial set of the measurement when docked to the docking station (e.g. numerical value), thereby freeing up display space on the handheld monitor's display for additional uses, such as, for example, increasing the size of the measurements displayed or displaying other parameters. The remaining measurements (e.g. waveform) can be displayed on the docking station display 1705. A measurement can be uniquely displayed either on the docking station display or on the handheld monitor display. The additional display space can be used for enlarging the partial measurement (e.g. numerical value) on the portable monitor to increase readability, showing the partial measurement in greater detail, and/or displaying an additional measurement.

Figure 18:
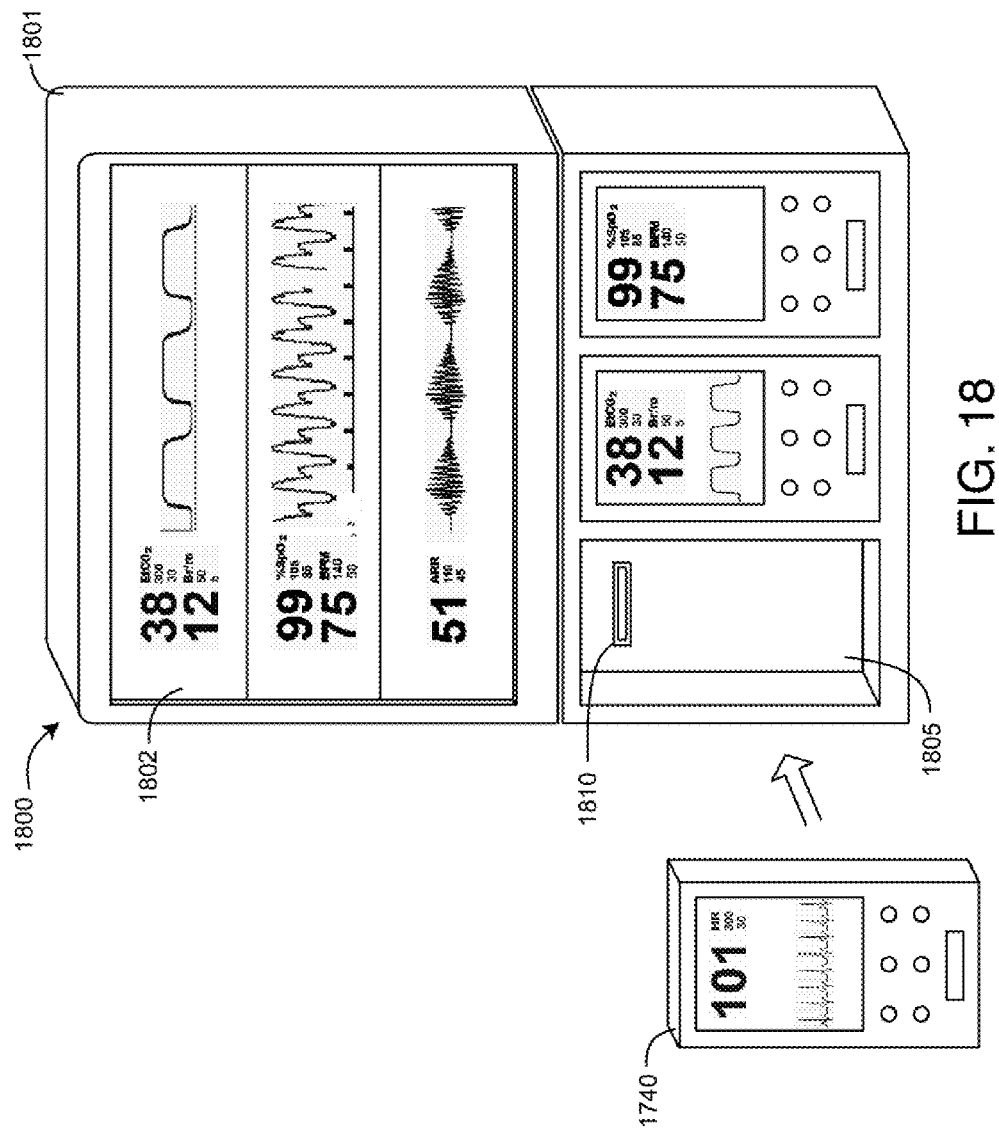
FIG. 18 illustrates a perspective view of another embodiment of a modular patient monitor having a docking station.

FIG. 18 illustrates a perspective view of another embodiment of a modular patient monitor 1800 having a docking station 1801. In the illustrated embodiment, docking station includes a display 1802 and three docking ports 1805 for receiving three handheld monitors. One handheld monitor 1740 is shown in its independent configuration. The handheld monitor 1740 can mechanically attach to the docking port 1805 and/or electrically attach to the docking station 1801 via an electrical and/or data port 1810. In one embodiment, patient data, such as measurements of physiological parameters, can be transferred between the docking station and portable monitor through the data port in either direction. In some embodiments, the docking station can provide electrical power to the handheld monitor and/or charge the handheld monitor's battery.

Data can also be transmitted between individual handheld monitors 1740 through a data connection. The data can be transferred from one monitor through the docking station's data port 1810 to the docking station 1801 and then to another handheld monitors. In one embodiment, a cable can be used to connect an input on one monitor to an output on another monitor, for a direct data connection. Data can also be transmitted through a wireless data connection between the docking station and handheld monitors and/or between individual monitors. In some embodiments, the docking station can further analyze or process received data before transmitting the data. For example, the docking station can analyze data received from one or more monitors and generate a control signal for another monitor. The docking station can also average, weight and/or calibrate data before transmitting the data to a monitor.

Data from other handheld monitors can be used to improve the measurements taken by a particular monitor. For example, a brain oximetry monitor can receive patient data from a pulse oximetry monitor, or vice versa. Such data can be used to validate or check the accuracy of one reading against another, calibrate a sensor on one monitor with measurements taken from a sensor from another monitor, take a weighted measurement across multiple sensors, and/or measure the time lapse in propagation of changes in a measured physiological parameter from one part of the body to another, in order, for example, to measure circulation. In one example, a monitor can detect if the patient is in a low perfusion state and send a calibration signal to a pulse oximetry monitor in order to enhance the accuracy of the pulse oximetry measurements. In another example, data from a pulse oximetry monitor can be used as a calibration signal to a blood pressure monitor. Methods and systems for using a non-invasive signal from a non-invasive sensor to calibrate a relationship between the non-invasive signal and a property of a physiological parameter are described in U.S. Pat. No. 6,852,083, titled System and Method of Determining Whether to Recalibrate a Blood Pressure Monitor, issued Feb. 8, 2005, incorporated by reference herein in its entirety.

Figure 19:
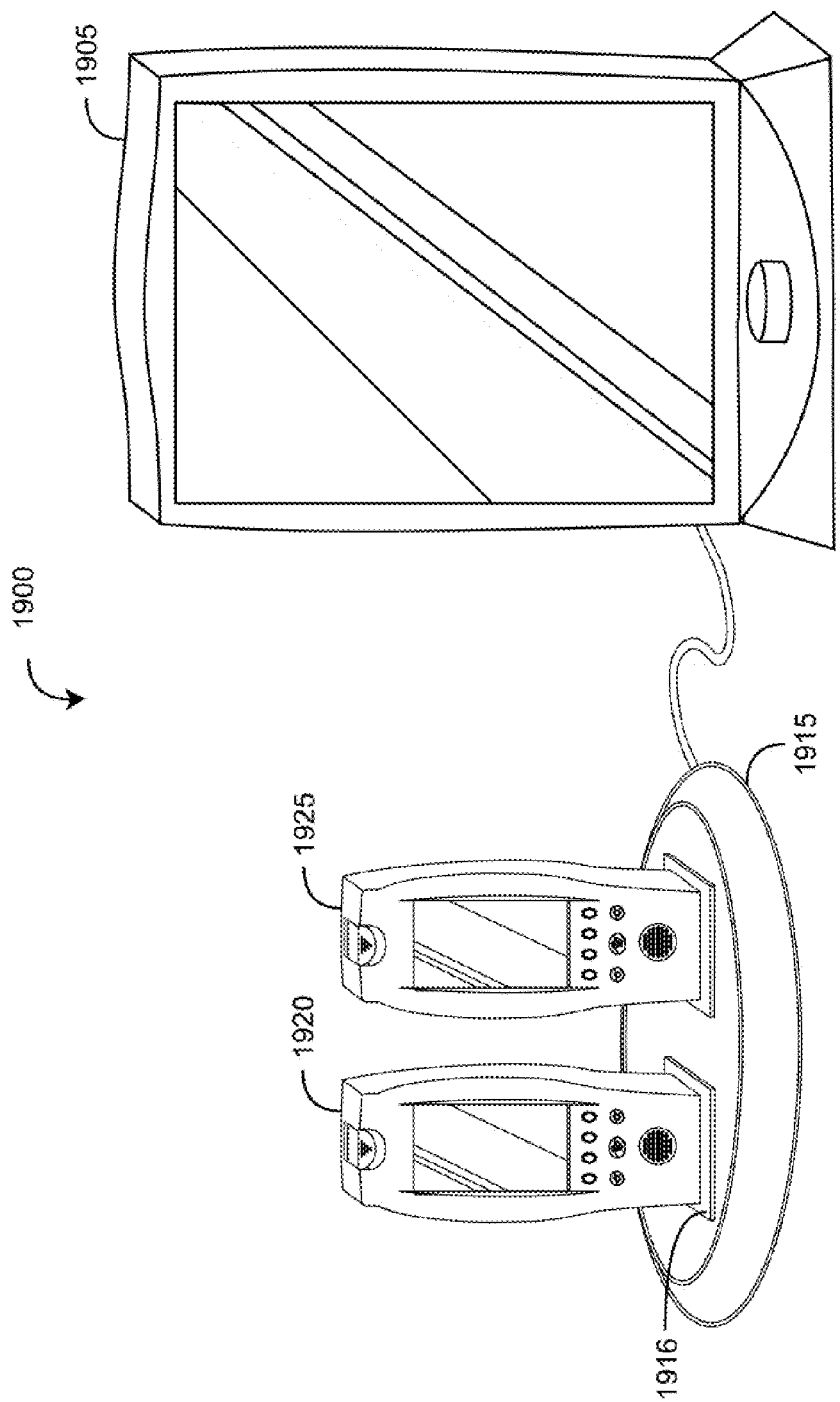
FIG. 19 illustrates a perspective view of an embodiment of a modular patient monitor having an external, attachable docking base.

FIG. 19 illustrates a perspective view of an embodiment of a modular patient monitor 1900 having a patient monitor 1905 and an external, attachable docking base 1915 having docking ports 1916 for receiving portable monitors 1920, 1925. In some embodiments, the docking base can have docking ports for any number of portable monitors. The docking base can be connected to the patient monitor through a communication medium, such as wirelessly or through a wire. The docking base can be positioned such that a user can view both the handheld monitor displays and patient monitor display simultaneously. In some embodiments, measurements of physiological parameters can be spanned over the handheld monitor displays and patient monitor display.

Figure 20:
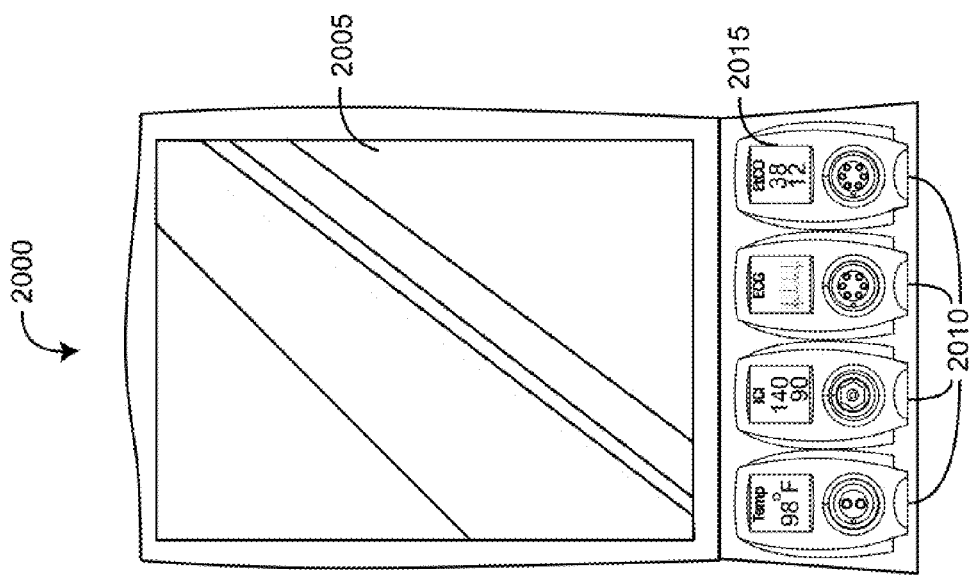
FIG. 20 illustrates a front view of an embodiment of a patient monitor having docking ports for parameter cartridges.

FIG. 20 illustrates a front view of an embodiment of a patient monitor 2000 having docking ports for parameter cartridges 2010. The patient monitor can have one or more docking ports for one or more parameter cartridges. In the illustrated embodiment, a parameter cartridge includes a display 2015 for displaying a measurement of the parameter. For example, a temperature cartridge can display the patient's temperature on its own display. In some embodiments, measurements can be spanned across the patient monitor display 2005 and one or more of the cartridge displays 2015.

Furthermore, in certain embodiments, the systems and methods described herein can advantageously be implemented using computer software, hardware, firmware, or any combination of software, hardware, and firmware. In one embodiment, the system includes a number of software modules that comprise computer executable code for performing the functions described herein. In certain embodiments, the computer-executable code is executed on one or more general purpose computers or processors. However, a skilled artisan will appreciate, in light of this disclosure, that any module that can be implemented using software can also be implemented using a different combination of hardware, software or firmware. For example, such a module can be implemented completely in hardware using a combination of integrated circuits. Alternatively or additionally, such a module can be implemented completely or partially using specialized computers or processors designed to perform the particular functions described herein rather than by general purpose computers or processors.

Moreover, certain embodiments of the invention are described with reference to methods, apparatus (systems) and computer program products that can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the acts specified herein to transform data from a first state to a second state.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

A modular patient monitor has been disclosed in detail in connection with various embodiments. These embodiments are disclosed by way of examples only and are not to limit the scope of the claims that follow. One of ordinary skill in art will appreciate many variations and modifications. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein. One of ordinary skill in the art will appreciate the many variations, modifications and combinations. For example, the various embodiments of the patient monitoring system can be used with sensors that can measure any type of physiological parameter. In various embodiments, the displays used can be any type of display, such as LCDs, CRTs, plasma, and/or the like. Further, any number of handheld monitors can be used as part of the patient monitoring system.

What is claimed is:

1. A modular patient monitor comprising:
    a docking station having a housing, the docking station including an integrated first display, a docking station processor, and a handheld port, the docking station processor configured to provide patient monitoring functionality with respect to a first set of physiological parameters; and
    a handheld monitor removably attachable both mechanically and electrically to the docking station via the handheld port, the handheld monitor including a second display and a handheld monitor processor, the second display having a display area smaller than the first display, the handheld monitor processor configured to provide patient monitoring functionality with respect to a second set of physiological parameters,
    wherein if the handheld monitor is not docked to the docking station:
        the docking station processor is configured to cause at least some measurements of the first set of physiological parameters to be displayed on the first display, and
        the handheld monitor processor is configured to cause at least some measurements of the second set of physiological parameters to be displayed on the second display including a numerical portion at a first display size and a waveform portion extending through a first time period,
    wherein, in response to the handheld monitor being docked to the docking station:

the handheld monitor processor is configured to automatically transmit measurements of the second set of physiological parameters to the docking station processor, the docking station processor is configured to automatically cause at least some measurements of the second set of physiological parameters to be displayed on the first display including the waveform portion extending through a second time period longer than the first time period, and the handheld monitor processor is configured to automatically cause the second display to display at least the numerical portion at a second display size larger than the first display size, and remove the waveform portion from the second display.

2. The modular patient monitor according to claim 1, wherein when the handheld monitor is docked to the docking station, the handheld monitor processor is further configured to automatically cause at least one measurement displayed on the first display to mirror a measurement on the second display.

3. The modular patient monitor according to claim 1, wherein when the handheld monitor is docked to the docking station, the handheld monitor processor is further configured to automatically cause at least one measurement displayed on the first display or second display to be unique to that respective display.

4. The modular patient monitor according to claim 1, wherein the first set of physiological parameters and the second set of physiological parameters have at least some common parameters.

5. The modular patient monitor according to claim 1, wherein the first set of physiological parameters provides a different measurement than the second set of physiological parameters.

6. The modular patient monitor according to claim 1, wherein the measurements of the first set of physiological parameters are displayed in at least one of a waveform or a numerical value.

7. The modular patient monitor according to claim 1, wherein the handheld port is integrated to the docking station.

8. The modular patient monitor according to claim 1, wherein the handheld port is integrated to a docking base connected to the docking station.

9. The modular patient monitor according to claim 8, wherein the docking base is connected to the docking station through a communication medium.

10. The modular patient monitor according to claim 1, wherein:
the first set of physiological parameters is blood constituent related; and
the second set of physiological parameters is non-blood related.

11. The modular patient monitor according to claim 1, wherein the docking station further includes a second handheld port, and wherein the modular patient monitor further comprises:
a second handheld monitor removably attachable both mechanically and electrically to the docking station via at least one of the handheld port or the second handheld port, the second handheld monitor including a second handheld monitor processor and a third display, the third display having a display area smaller than the first display, the second handheld monitor processor configured to provide patient monitoring functionality with respect to a third set of physiological parameters, wherein if the second handheld monitor is not docked to the docking station, the second handheld monitor processor is configured to cause at least some measurements of the third set of physiological parameters to be displayed on the third display including a second numerical portion at a third display size and a second waveform portion extending through a third time period, wherein, in response to the second handheld monitor being docked to the docking station:
the second handheld monitor processor is configured to automatically transmit measurements of the third set of physiological parameters to the docking station processor, the docking station processor is configured to automatically cause at least some measurements of the third set of physiological parameters to be displayed on the first display including the second waveform portion extending through a fourth time period longer than the third time period, and the second handheld monitor processor is configured to automatically cause the third display to display at least the second numerical portion at a fourth display size larger than the third display size, and remove the second waveform portion from the third display, wherein the handheld monitor is further removably attachable both mechanically and electrically to the docking station via at least one of the handheld port or the second handheld port.

12. The modular patient monitor according to claim 11, wherein the display area of the third display is the same as the display area of the second display.

13. The modular patient monitor according to claim 1, wherein further in response to the handheld monitor being docked to the docking station:
the handheld monitor processor is further configured to automatically transmit measurements of a second parameters to the docking station processor, the second parameter being one of the second set of physiological parameters the handheld parameter is capable of monitoring, the handheld monitor processor is further configured to automatically cause display of the measurements of the second parameter on the second display at a first level of detail, the docking station processor not being configured to monitor the second parameter when the handheld monitor is not docked, and the first display of the docking station is changed by the docking station processor so as to display the measurements of the second parameter at a second level of detail greater than the first level of detail.

14. The modular patient monitor according to claim 1, wherein, further in response to the handheld monitor being docked to the docking station, the docking station processor is further configured to automatically auto-scale the at least some measurements of the first set of physiological parameters displayed on the first display to make room for the displayed measurements of the second set of physiological parameters.

15. The modular patient monitor according to claim 14, wherein the second display size substantially fills the display area of the second display.

16. A method for displaying measurements of physiological parameters, the method comprising:
receiving first patient data at a docking station and second patient data at a handheld monitor, the docking station including a first display and a docking station processor, the handheld monitor including a handheld monitor processor and a second display having a display area smaller than the first display, the docking station processor configured to provide patient monitoring functionality with respect to at least a first parameter of the first patient data, the handheld monitor processor configured to provide patient monitoring functionality with respect to at least a second parameter of the second patient data, the docking station and the handheld monitor configured such that the handheld monitor may be docked to, or undocked from, the docking station;

if the handheld monitor is undocked from the docking station:
automatically displaying, by the docking station processor, at least some measurements of the first parameter on the first display, and
automatically displaying, by the handheld monitor processor, at least some measurements of the second parameter on the second display, the at least some measurements of the second parameter including a numerical portion at a first display size and a waveform portion extending through a first time period; and in response to the handheld monitor being docked to the docking station:
automatically transmitting, by the handheld monitor processor, measurements of the second set of physiological parameters to the docking station processor,
automatically displaying on the first display, and by the docking station processor, at least some measurements of the second parameter including the waveform portion extending through a second time period longer than the first time period, and
automatically displaying on the second display, and by the handheld monitor processor, at least the numerical portion at a second display size larger than the first display size, and
automatically remove, by the handheld monitor processor, the waveform portion from the second display.

17. The method according to claim 16, wherein the docking station does not monitor the second parameter when the handheld monitor is not docked.

18. The method according to claim 17, wherein the measurements of the first parameter are displayed in at least one of a waveform or a numerical value.

19. The method according to claim 17, wherein when the handheld monitor is docked to the docking station, at least some measurements of the second parameter are at least partially displayed simultaneously on the second display and the first display.

20. The method according to claim 17, wherein when the handheld monitor is docked to the docking station, at least a portion of the measurements of the second parameter are displayed uniquely on the second display or the first display.

* * * * *

UNITED STATES PATENT AND TRADEMARK OFFICE
CERTIFICATE OF CORRECTION

| | | |
|---|---|---|
| PATENT NO. | : 9,161,696 B2 | Page 1 of 1 |
| APPLICATION NO. | : 12/641087 | |
| DATED | : October 20, 2015 | |
| INVENTOR(S) | : Al-Ali et al. | |

It is certified that error appears in the above-identified patent and that said Letters Patent is hereby corrected as shown below:

In the Specification

In column 1 at line 26, Change "(SpO2)," to --(SpO$_2$),--.

In column 1 at line 57, Change "CO2" to --CO$_2$--.

In column 2 at line 55, Change "station." to --station;--.

In column 3 at line 31, Change "10)." to --1D).--.

Signed and Sealed this
Seventh Day of June, 2016

Michelle K. Lee
*Director of the United States Patent and Trademark Office*